US012676230B2

(12) United States Patent
Lima et al.

(10) Patent No.: US 12,676,230 B2
(45) Date of Patent: Jul. 7, 2026

(54) FLAP PREDICTION SYSTEM BASED ON VOLUMETRIC DATA AND FOUNDATION MODELS

(71) Applicant: MICROSOFT TECHNOLOGY LICENSING, LLC, Redmond, WA (US)

(72) Inventors: Andréa Britto Mattos Lima, Sao Paulo (BR); Christopher Patrick O'Dowd, Seattle, WA (US); Spencer G. Fowers, Duvall, WA (US); Thiago Vallin Spina, Campinas (BR)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 131 days.

(21) Appl. No.: 18/202,850

(22) Filed: May 26, 2023

(65) Prior Publication Data

US 2024/0395392 A1    Nov. 28, 2024

(51) Int. Cl.
*G16H 30/40*        (2018.01)
*G16H 10/60*        (2018.01)

(52) U.S. Cl.
CPC ............. *G16H 30/40* (2018.01); *G16H 10/60* (2018.01)

(58) Field of Classification Search
CPC ........ G16H 30/40; G16H 10/60; G16H 20/40; G16H 30/20; G16H 40/67; G16H 50/20; G16H 50/50; G16H 50/70; A61B 2017/00792; A61B 2034/105;
(Continued)

(56) References Cited

U.S. PATENT DOCUMENTS

2017/0340390 A1* 11/2017 Harbison ................ G06T 19/20
2019/0282300 A1*  9/2019 Sayadi ................... A61B 34/10

FOREIGN PATENT DOCUMENTS

WO        2022261528 A1    12/2022

OTHER PUBLICATIONS

Validating machine learning approaches for prediction of donor related complication in microsurgical breast, Myung et al. (Year: 2021).*

(Continued)

*Primary Examiner* — Chinyere Mpamugo
(74) *Attorney, Agent, or Firm* — Newport IP, LLC; Jacob P. Rohwer

(57)        ABSTRACT

Disclosed are techniques for an artificial intelligence (AI) based recommendation system associated with treatment of a patient. The AI based recommendation system can be configured to receive three-dimensional (3D) image data that is associated with a patient, where the 3D image data includes volumetric data; and detect one or more anatomical treatment sites associated with the patient. The 3D image data may further be annotated with one or more of the detected anatomical treatment sites. By leveraging a foundation model with detailed context on flap harvesting, the AI based recommendation system may evaluate the annotated 3D image data, identify viable donor sites for flap harvesting, and provide recommendations for one or more viable donor sites for flap harvesting based on a treatment criteria for treatment of the patient. The recommendation may be evaluated and further refined by additional user based interaction with the AI based system.

16 Claims, 11 Drawing Sheets

AI BASED RECOMMENDATION SYSTEM

(58) Field of Classification Search
CPC ........ A61B 34/10; G06N 20/00; G06N 3/045;
G06N 3/08; G06T 7/0012
See application file for complete search history.

(56) References Cited

OTHER PUBLICATIONS

International Search Report and Written Opinion received for PCT
Application No. PCT/US2024/026122, Aug. 20, 2024, 15 pages.
International Preliminary Report on Patentability (Chapter I) received
for PCT Application No. PCT/US2024/026122, Dec. 11, 2025, 10
pages.

* cited by examiner

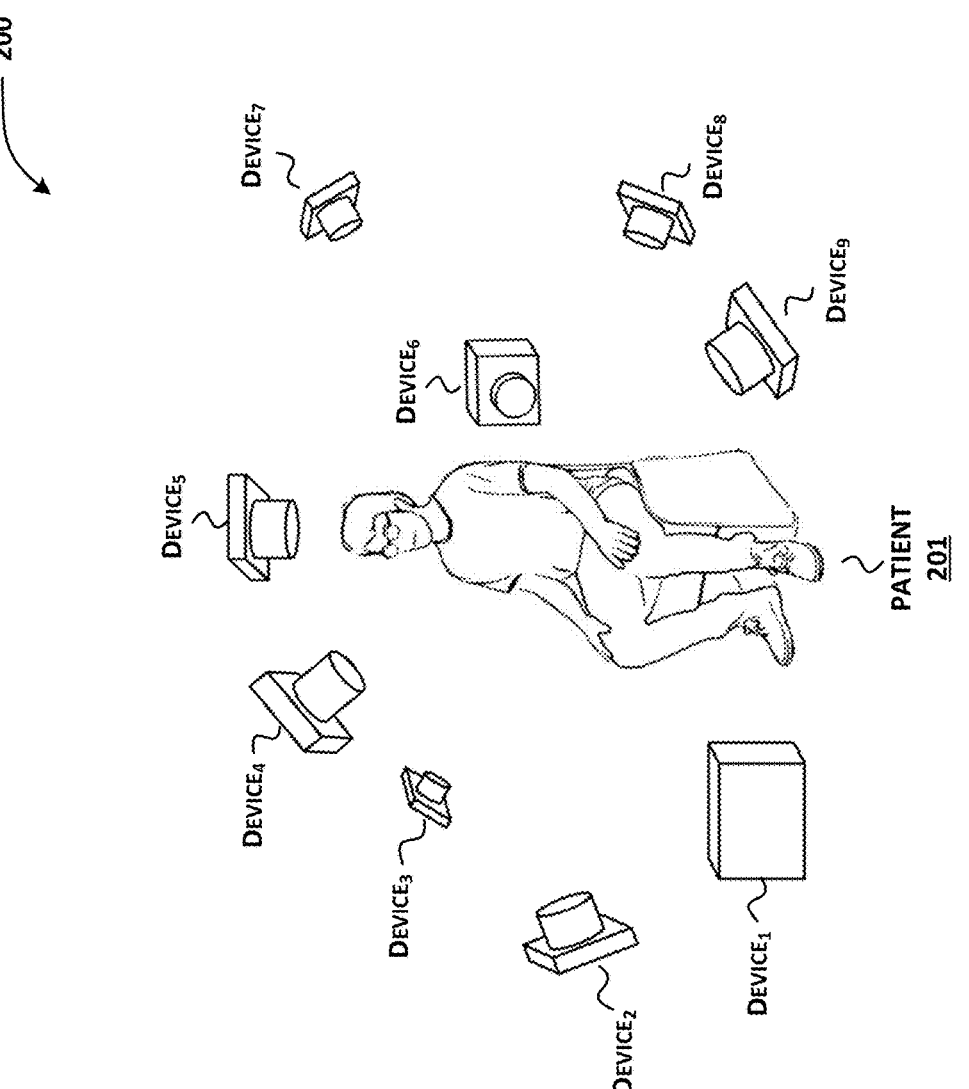
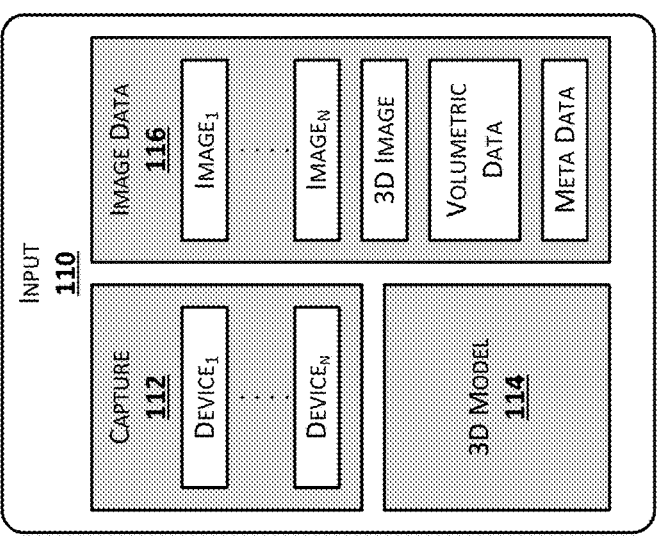
FIG. 2

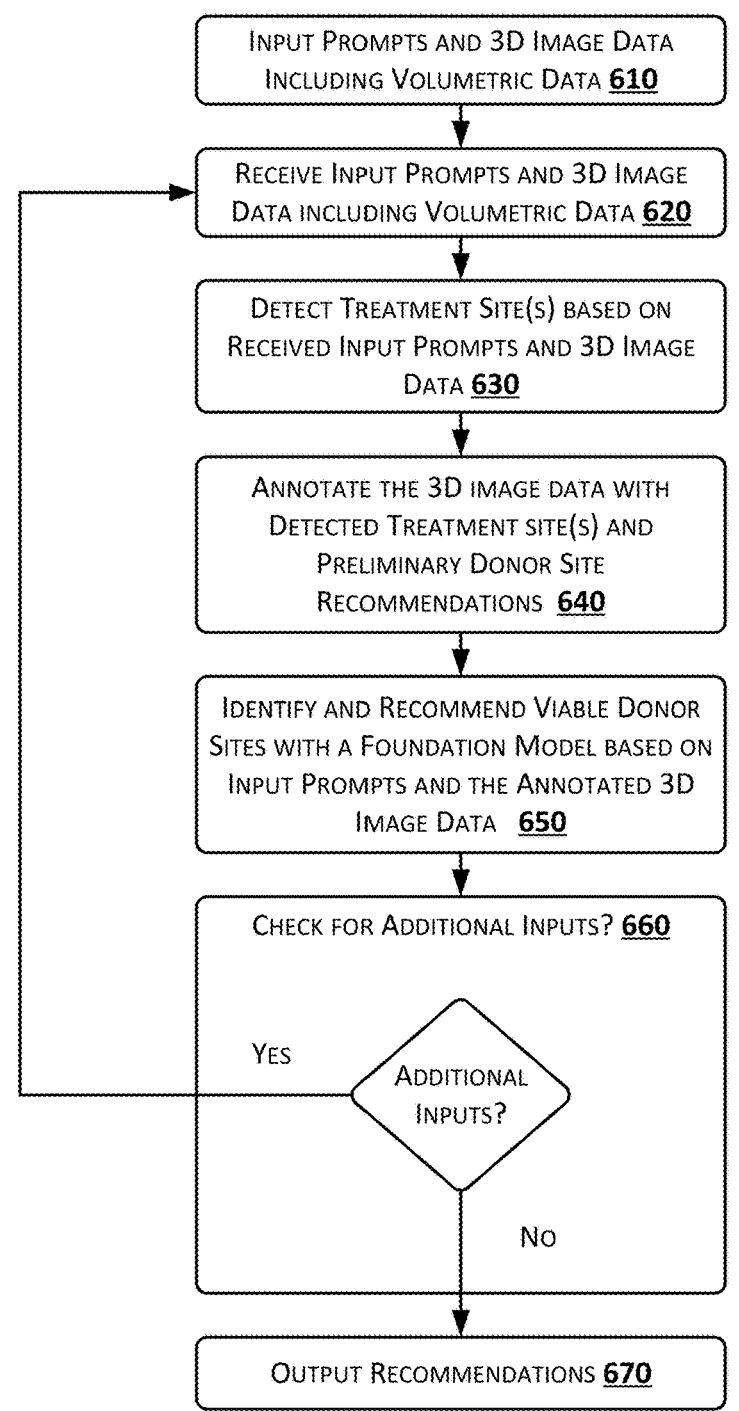
FIG. 6

700

INPUT PROMPTS 610

SELECT TREATMENT CRITERIA 612

COLLECT PATIENT MEDICAL RECORDS 614

CAPTURE IMAGES OF PATIENT WITH VOLUMETRIC DATA 616

RECEIVE INPUTS 620

PROVIDE INPUT PROMPTS TO FOUNDATION MODEL WITH 3D IMAGES AND VOLUMETRIC DATA 622

PROVIDE INPUT PROMPTS TO MEDICAL PROFESSIONAL WITH 3D IMAGES AND VOLUMETRIC DATA 624

DETECT TREATMENT SITES BASED ON RECEIVED INPUT PROMPTS AND 3D IMAGE DATA 630

Figure 11:
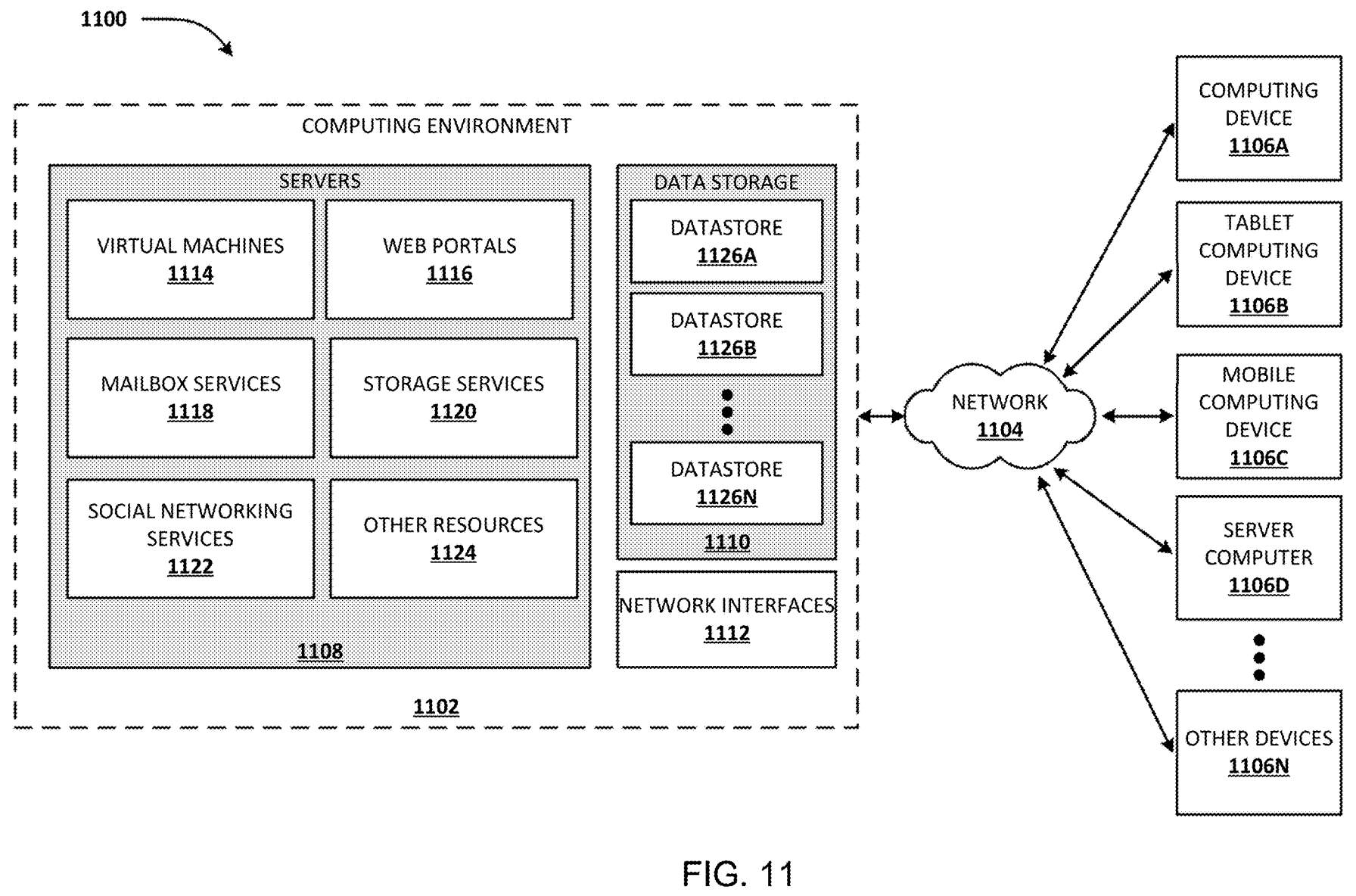

COMPUTING DEVICE 1106A

TABLET COMPUTING DEVICE 1106B

MOBILE COMPUTING DEVICE 1106C

SERVER COMPUTER 1106D

OTHER DEVICES 1106N

NETWORK 1104

COMPUTING ENVIRONMENT

DATA STORAGE

DATASTORE 1126A

DATASTORE 1126B

DATASTORE 1126N

1110

NETWORK INTERFACES 1112

SERVERS

VIRTUAL MACHINES 1114

WEB PORTALS 1116

MAILBOX SERVICES 1118

STORAGE SERVICES 1120

SOCIAL NETWORKING SERVICES 1122

OTHER RESOURCES 1124

FLAP PREDICTION SYSTEM BASED ON VOLUMETRIC DATA AND FOUNDATION MODELS

BACKGROUND

Artificial intelligence (AI) has a rich history, dating back to the mid-20th century when pioneers like John McCarthy and Marvin Minsky first began exploring the concepts. Initially, AI was seen as a way to replicate human intelligence in machines, and early efforts focused on developing systems that could perform tasks like playing chess or proving mathematical theorems.

Over the years, AI has evolved and expanded its focus to include a wide range of applications, from image recognition to natural language processing (NLP). Various AI systems and methods may now be applied in numerous domains.

Large language models (LLMs) are a recent development in the field of NLP. LLMs can apply deep learning algorithms, sometimes referred to as machine learning (ML), to leverage massive amounts of data, which can result in highly accurate language processing capabilities. Some example LLMs include GPT-3 and BERT, which are trained on vast amounts of text data, allowing them to model complex relationships in language and highly accurate predictions for a wide range of language tasks such as: translation, summarization, and responses to questions. This has led to breakthroughs in areas like chatbots, virtual assistants, and language-based systems.

It is with respect to these and other considerations that the disclosure made herein is presented.

SUMMARY

Disclosed are techniques for an artificial intelligence (AI) based recommendation system associated with treatment of a patient. The AI based recommendation system can be configured to receive three-dimensional (3D) image data that is associated with a patient, where the 3D image data includes volumetric data; and detect one or more anatomical treatment sites associated with the patient. The 3D image data may further be annotated with one or more of the detected anatomical treatment sites. By leveraging a foundation model with detailed context on flap harvesting, the AI based recommendation system may evaluate the annotated 3D image data, identify viable donor sites for flap harvesting, and provide recommendations for one or more viable donor sites for flap harvesting based on a treatment criteria for treatment of the patient. The recommendation may be evaluated and further refined by additional user based interaction with the AI based system.

In some embodiments, a method for an artificial intelligence (AI) based recommendation system associated with care or treatment of a patient is disclosed, the method comprising: receiving three-dimensional image data associate with the patient, wherein the 3D image data includes volumetric data; detecting one or more anatomical treatment sites associated with the patient based on the received 3D image data; annotating the 3D image data with one or more of the detected anatomical treatment sites associated with the patient; evaluating the 3D image data with a foundation model to identify viable donor sites for flap harvesting; and providing a recommendation with the foundation model, where the recommendation includes one or more of the viable donor sites identified for flap harvesting based on a treatment criteria associated with treatment of the patient.

In various embodiments, a computer-readable storage medium having computer-executable instructions stored thereupon is described that, when executed by one or more processing units of an AI based recommendation system associated with care or treatment of a patient, cause the AI based processing recommendation system to: receive three-dimensional (3D) image data associate with the patient, wherein the 3D image data includes volumetric data; detect one or more anatomical treatment sites associated with the patient based on the received 3D image data; annotate the 3D image data with one or more of the detected anatomical treatment sites associated with the patient; evaluate the 3D image data with a foundation model to identify viable donor sites for flap harvesting; and provide a recommendation with the foundation model, where the recommendation includes one or more of the viable donor sites identified for flap harvesting based on a treatment criteria associated with treatment of the patient.

In still other embodiments, an AI based recommendation system associated with care or treatment of a patient is described, the AI based recommendation system comprising: a processor; and a computer-readable storage medium having computer-executable instructions stored thereupon that, when executed by the processor, cause the AI based recommendation system to: receive three-dimensional (3D) image data associate with the patient, wherein the 3D image data includes volumetric data; detect one or more anatomical treatment sites associated with the patient based on the received 3D image data; annotate the 3D image data with one or more of the detected anatomical treatment sites associated with the patient; evaluate the 3D image data with a foundation model to identify viable donor sites for flap harvesting; and provide a recommendation with the foundation model, where the recommendation includes one or more of the viable donor sites identified for flap harvesting based on a treatment criteria associated with treatment of the patient.

Various technical differences and benefits are achieved by the described systems and methods. For example, the presently described systems and methods are able to provide improved accuracy and reliability in medical recommendations by leveraging LLM's access to numerous skills and resources to process queries, and rank recommendations based on a criteria. The overall efficiency of generating, executing, testing, and validating multiple prompts can thus provide for improved accuracy, which may also omit wasted time exploring inaccurate solutions, and thus improve processing time by eliminating unnecessary review cycles.

In AI systems, such as LLM and ML based systems, the applicability domain refers to the range of inputs or situations in which a model is expected to perform well. The applicability domain can be influenced by factors such as the quality and quantity of data available, the complexity of the problem, the algorithms and models used by the AI system, and the level of human intervention and oversight. The applicability domain may also identify scenarios where the model's predictions are reliable and accurate, as well as scenarios where the model may struggle to deliver accurate results. Understanding the applicability domain is critical for AI practitioners and users, as it can help to identify potential risks and limitations of the model, and ensure that it is only used in scenarios where it is most effective. The presently described AI model has applicability over multiple domains, including but not limited to, imaging and video recognition, which may further be applicable to manufacturing, health care and medical diagnostic recommendation systems, and virtual assistants, to name a few.

In one example, an applicability domain may include AI systems that may be leveraged to identify trends in manufacturing to predict and reduce possible manufacturing problems. For example, a goal may be to evaluate 3D images of products and prevent manufacturing defects by applying a foundation model that monitors relevant factors such as stress points in materials, temperature gradients and heat dissipation. The applicability domain for this problem could be defined by the range of conditions under which the machine learning model is expected to perform accurately, and outside of which its predictions may be unreliable or incorrect. These conditions may include changes or shifts in materials, part failures, and excessive heat. Understanding and defining the applicability domain for this problem is important to ensure that the models can be used effectively for methods of manufacturing, planning, process controls and quality control.

Another applicable domain for the AI system may be in the field of virtual assistants, specifically in assisting medical professionals in identifying viable sites for tissue extraction or harvesting. The AI system could be used to scan 3D images, and generate multiple prompts or hints to guide medical professionals in a pre-surgical consultation with step-by-step explanations or alternative approaches. In one example, the AI system may guide the medical professional in capturing 3D images of a patient, marking the 3D images with annotation, and identifying treatment sites and/or tissue donor sites in the 3D images. The AI system may also provide ranked recommendations for viable donor sites, where the medical professional may provide feedback to the AI system to further focus or guide the recommendations. In some examples, the AI system may present the ranked recommendations in the form of text; while in other examples the AI system may present visual images (e.g., 3D images) that may be marked or annotated by the AI system to guide the medical profession. The applicability domain in this case could encompass various levels of medical education, ranging from elementary to advanced medical diagnosis, and could be tailored to specific topics such as defect detection, donor tissue site identification, and flap harvesting.

Features and technical benefits other than those explicitly described above will be apparent from a reading of the following Detailed Description and a review of the associated drawings. This Summary is provided to introduce a selection of concepts in a simplified form that are further described below in the Detailed Description. This Summary is not intended to identify key or essential features of the claimed subject matter, nor is it intended to be used as an aid in determining the scope of the claimed subject matter. The term "techniques," for instance, may refer to system(s), method(s), computer-readable instructions, module(s), algorithms, hardware logic, and/or operation(s) as permitted by the context described above and throughout the document.

BRIEF DESCRIPTION OF THE DRAWINGS

The Detailed Description is described with reference to the accompanying figures. In the figures, the left-most digit(s) of a reference number identifies the figure in which the reference number first appears. The same reference numbers in different figures indicate similar or identical items. References made to individual items of a plurality of items can use a reference number with a letter of a sequence of letters to refer to each individual item. Generic references to the items may use the specific reference number without the sequence of letters.

FIG. 2 illustrates a detailed portion of another example AI based recommendation system that is capable of implementing aspects of the techniques and technologies presented herein.

FIG. 6 illustrates is an example flow diagram for aspects of an AI based recommendation system, in accordance with various aspects described herein.

FIG. 7 illustrates is a detailed portion of a flow diagram for aspects of an AI based recommendation system, in accordance with various aspects described herein.

FIG. 11 is a diagram illustrating a distributed computing environment capable of implementing aspects of the techniques and technologies presented herein.

DETAILED DESCRIPTION

Figure 1:
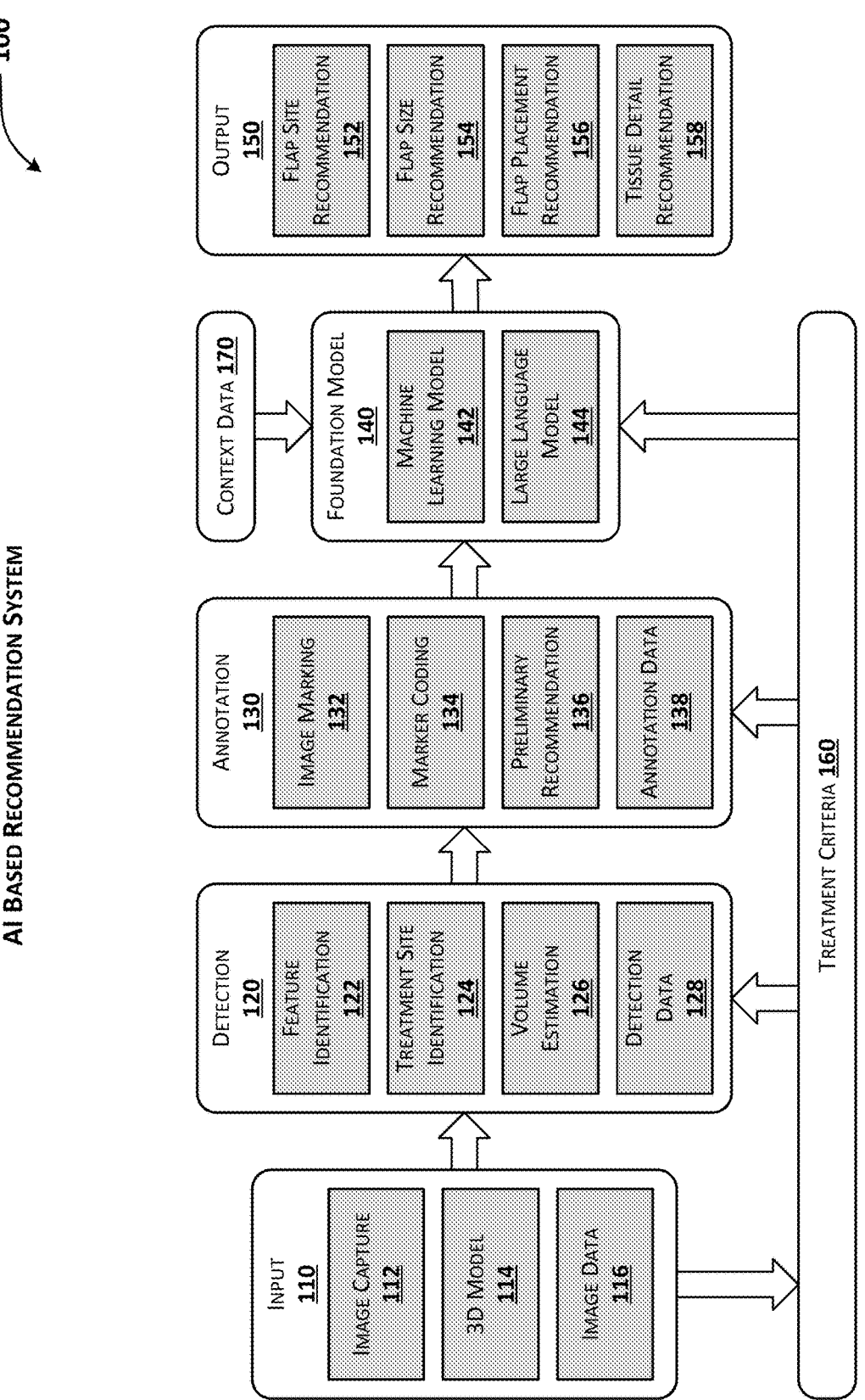
FIG. 1 illustrates an example AI based recommendation system that is capable of implementing aspects of the techniques and technologies presented herein.

The present disclosure presents techniques for an artificial intelligence (AI) based recommendation system associated with treatment of a patient. The AI based recommendation system can be configured to receive three-dimensional (3D) image data that is associated with a patient, where the 3D image data includes volumetric data; and detect one or more anatomical treatment sites associated with the patient. The 3D image data may further be annotated with one or more of the detected anatomical treatment sites. By leveraging a foundation model with detailed context on flap harvesting, the AI based recommendation system may evaluate the annotated 3D image data, identify viable donor sites for flap harvesting, and provide recommendations for one or more viable donor sites for flap harvesting based on a treatment criteria for treatment of the patient. The recommendation may be evaluated and further refined by additional user based interaction with the AI based system. Additional technical differences and benefits will be realized in light of the present disclosure.

In medicine, the term "flap" usually refers to a piece of tissue that is moved from one part of the body to another, usually for the purpose of reconstructive surgery. A "flap" can be composed of a tissue, including any number of related connective tissues or portions of tissues. Example "tissues" may include, but are not limited to, skin, muscle, fat, bone or skeletal support, nerves, ligaments, blood vessels, or a combinations of these tissues. The surgical site of the patient can be referred to as a treatment site or a defect site in the case of non-aesthetic. The flap site of the patient can be referred to as a donor site.

Reconstructive surgery may be desired for a number of reasons, including both elective and non-elective surgical procedures. Some surgical procedures may be for cosmetic or non-health related reasons, such as in the case of some plastic surgery; while some non-elective surgical procedures may be to improve the health and quality of life of the patient. In some examples, reconstructive surgery may be to improve a patient's physical appearance due to a birth defect, such as in the case of a cleft palate or cleft lip, which are typically more than a simple cosmetic repair. A variety of other examples are also contemplated as reconstructive surgery, both cosmetic or non-cosmetic based, such as reconstructive surgery for abnormal structures or anomalies due to injury, trauma, infection, birth defects, congenital malformations, disease, tumors, or age.

Planning a flap surgery can be a complex process. The treatment site of the patient is first evaluated to define the treatment objectives, which may include structural, aesthetic, and/or functional objectives. Then, the treatment site is further analyzed to determine the requirements for a viable donor site, which may include specific tissue requirements such as bone, scaffolding, blood vessels, nerves, ligaments, and other such requirements. Possible (or candidate) donor sites can then be identified that satisfy both the treatment objectives of the surgical procedure and requirements for viable donor sites.

Example structural treatment objectives may include structural repair or reconstruction of damaged areas, or structural formation of missing structures that may have resulted from congenital defects. An aesthetic reconstruction may further require reshaping structural supports by either reducing material from existing structures, adding material to supplement or augment existing structures, or combinations thereof. In some examples, the structural objectives may be refined based on functional requirements such as blood flow requirements, airflow requirements, muscular and skeletal range of motion and movement, movement, for breathing or speaking, Requirements for viable donor sites may vary based on the location of the treatment site on the patient, the volume of tissue required for the treatment, as well as other requirements such as blood flow and structural support, as previously discussed. The viability of candidate donor sites are not uniformly determined for all patients, and thus may vary from patient to patient based on their personal anatomical differences.

The location of a donor flap site can be manifested multiple ways. A "local flap" involves the movement of tissue from a donor site that is adjacent the treatment site, where a portion of the tissue may remain attached at one end so that the blood flow, nerve endings, and other critical functions remain attached with minimal disruption. A "regional flap" involves the movement of donor tissue from a nearby region of the treatment site that is attached to a specific functional element such as a nerve, blood vessel or ligament; where the specific function remains intact. A "Free flap" involves the movement of tissue from a distant donor site, which is detached from its original functionality of blood supply, never or tissue, and then reattached to provide the same functionality at the treatment site.

In this present disclosure, an artificial intelligence (AI) based recommendation system is described that can perform a volumetric capture of a patient that is the subject of reconstructive surgery (e.g., using Microsoft's Holoportation™ technology), and use Foundation models to predict and recommend the optimal donor flap size and placement for the treatment of the patient based on anatomical data and the patient 3D image data that is input. Conversational AI interaction via a chatbot (e.g., see FIG. 5) may also be leveraged to further guide and modify the recommendations based on various treatment criteria that may be recommended, such as by a medical professional. Also, the AI system may present recommendations in the form of text, visual images (e.g., 3D images), or combinations thereof; where the visual images may be marked or annotated by the AI system to guide the medical profession on the donor flap location, size, and placement.

A general procedural flow that may be employed by the AI based recommendation system 100, is as follows. A volumetric scan of the patient is first performed, either guided by an AI based system or separately therefrom. The system, either with or without assistance from a human operator, estimates the volume of a treatment site of the patient (which may correspond to an injury or another anomaly) and the AI based recommendation system applies generative models to provide guidance on the optimal flap size and placement based on the patient's anatomy, the location and extent of any defective or missing tissue, and other relevant factors such as better functional and/or aesthetic outcomes. The AI recommendation system can thus help the medical professional (e.g., a surgeon) decide whether to use a local flap, a regional flap, or a free flap based on the size, location, and characteristics of the defective or missing tissue. The system can also provide guidance on the best way to handle the tissue flap to ensure optimal blood flow and healing. For example, the system may assist a surgeon in determining the optimal placement and orientation of the flap, the best way to suture the flap into place, and other important details.

The various functional blocks described below provide non-limiting illustrative examples of AI based recommendation system implementations, as well as procedural flows and other details.

FIG. 1 illustrates an example AI based recommendation system 100 that is capable of implementing aspects of the techniques and technologies presented herein. As illustrated the example system 100 includes an input component 110, a detection component 120, an annotation component, an AI system component 140, an output component 150, a treatment criteria 160 and context data 170.

The input component 110 includes functional blocks for image capture 112, a three-dimensional (3D) model 113, and image data 116. Operationally, the input component 110 is configured to capture various images of a patient, either with or without human assistance. The captured images may be referred to as image data 116. The image data 116 can be applied to the 3D model 114, which may result in generation of additional image data 116 (e.g., 3D images) that includes volumetric data, as will be further described herein. The image data 116 in various examples may be captured by various image sensor type of devices such as digital cameras, digital video, analog cameras, analog video, and the like. The image sensors are physically oriented in a 3D space about a patient to capture a variety of angles, positions, and fields of view, as may be required to achieve a 3D model 114 of the patient with sufficient volumetric information to be processed by the AI based recommendation system 100. Image data 116 may be provided to one or more of the detection component 120, the annotation component 130, the foundation model 140 and the output component 150.

Input component 110 may also be configured to identify a treatment criteria 160. The treatment criteria 160 may be identified with or without human assistance. That is to say, the treatment criteria 160 may be recommended by an AI based system, by a human operator (e.g., medical professional), or by a combination of a human operator with assistance from an AI based system. For purposes of this disclosure, the term "medical professional" and "human operator" may be used interchangeably. The term human operator may refer to, but is not limited to, any variety of human operator such as a doctor, a nurse, a technician, an assistant, or a medical specialist such as surgeon, dermatologist, pathologist, plastic surgeon, podiatrist, etc.

Treatment criteria 160 may correspond to a functional objective, an aesthetic objective, a risk factor objective, or any combinations thereof. The treatment criteria may further include objectives to maximize or minimize a desired outcome. An example functional objective may be to facilitate improved physiological movement of the patient (e.g., a desired outcome to maximize movement) such as movement of limbs, joints, extremities, digits, toes, or other body parts. Another example functional objective may be to improve air flow or blood flow of the patient (e.g., a desired outcome to maximize flow) for improved breathing, circulation or delivery of oxygen and nutrients to the body. An example aesthetic objective may be to alter or reshape a treatment region (e.g., skeletal contouring) to increase (e.g., maximize) or reduce (e.g., minimize) the size of certain body features (e.g., nose, cheeks, chin, etc.) for a desired outcome with minimal scarring. In some examples, functional and aesthetic objectives may be linked such as in the case of a cleft palate or a deviated septum, where a restricted airflow may be improved with the same surgical procedure that improves an aesthetic appearance of the patient. Example risk factor objectives may include factors such as minimize surgical complexity, reduce healing time, reduce risk of death, reduce risk of impaired function, reduce risk of side-effects, etc.

Detection component 120 is illustrated as including functional blocks for feature identification 122, treatment site identification 124, volume estimation 126, and detection data 128. Operationally, the detection component 120 may be configured to evaluate the various captured images of the patient, either with or without human assistance. From the image data 116, feature identification 122 of the patient may be performed. Feature identification may include identification and/or labeling of various body parts and joints (e.g., head, neck, chest, shoulder, back, waist, arm, elbow, wrist, hand, finger, leg, knee, foot, toe, nose, mouth, brow, chin, eye, ear, etc.), and also identification of body part characteristics such as skin tone, hair, hair color, etc. Found or identified features may be compared or mapped to a 3D anatomical model. The detection component 120 may also be configured for treatment site identification 124, either with or without human assistance. In some examples, treatment site identification 124 may correspond to identification of an otherwise "normal" human anatomical region, where the treatment area may be designated for personal aesthetics or cosmetic reasons. In some other examples, treatment site identification 124 may correspond to identification of "defective" or "abnormal" regions, which may be considered abnormal structures or anomalies from what is expected in a typical human anatomical model. Such defects or anomalies may be due to patient injury, trauma, scars, growths, infection, birth defects, congenital malformations, disease, tumors, etc. Once a treatment site is identified for the patient, volume estimation 126 may be performed on the treatment site, either with or without human assistance. The identified features, defects or anomalies, and/or estimated volumes for the treatment site, may be referred to as detection data 128. Detection component 120 may also receive and/or process the treatment criteria 160 as part of the detection process; such as to focus on a specific type of defect, feature, or objective in treatment of the patient.

The annotation component 130 is illustrated as including functional blocks for image marking 132, marker coding 134, preliminary recommendation 136, and annotation data 138. Operationally, the annotation component 130 is configured to evaluate the various captured images 116 of the patient and any additional detection data 128, either with or without human assistance. From the image data 116 and the detection data 128, image marking 132 may be performed. Image marking may include annotation of one or more of the images with the locations or regions for each of the identified features, defects and/or treatment areas in the detection data 128. For example, the location of blood vessels, ligaments and nerves may be marked on the image, as well as a defect such as a tumor or deformed portion of a limb. Additionally, the image data may be annotated with possible (e.g., preliminary) donor tissue sites for extraction and/or harvesting. The markings on the images indicate the location and/or region of the identified features, defects, and/or possible donor sites so that they are clearly identifiable by a human operator.

The annotation component 120 may also be configured for marker coding 134 so that a coding scheme may be employed in the annotations (e.g., different colors or fill codes can indicate types of different features, defects or anomalies, or possible donor tissue sites). Preliminary recommendations 136 may include image markings, color codes or fill patterns, or other meta data including but not limited to text based notes. The described image markings, marker coding, and preliminary recommendations for the annotation component 130 may be referred to as annotation data 138. Annotation component 130 may also receive and/or process the treatment criteria 160 as part of the annotation process; such as to focus on a specific type of defect, feature, or donor region of the patient as specified in the treatment criteria 160.

One or more of the image data 116, the defect data 128, and/or the annotation data 138 may be provided to the foundation model component 140, which includes functional blocks for a machine learning model (ML) 142 and/or a large language model (LLM) 144. Operationally, the foundation model component 140 is configured to evaluate the various captured images of the patient from image data 116, the detection data 128, and the annotation data 130; and responsively apply a foundation model to generate a set of recommendations. Output component 160 illustrates the types of recommendations that are generally contemplated herein, as illustrated by functional blocks for a viable flap site recommendation 152, a flap size recommendation 154, a flap placement recommendation 156, and tissue detail recommendations 158.

Foundation models, such as large language models (LLMs), are trained on very large quantities of data, which is typically unlabeled data, and with minimally guided or self-supervised learning. The training process results in an AI system that is capable of handling a wide variety of tasks, including image classification, language processing such as NLP, which works with extreme accuracy in human guided tasks. The Foundation model is capable of analyzing far more medical data than a human counterpart, including things like vast amounts of medical treatment records, medical images, and annotations to medical images.

In the present disclosure, it is contemplated that the foundation model 140 may be seeded with large amounts of data to prompt and/or tune the AI based recommendation system 100 into making accurate recommendations on candidate surgical donor tissue sites to be harvested or extracted. For example, the foundation model may be seeded with the entire medical history of a patient, including prior captured images, prior captured medical data, as well as being seeded with an entire treatise on medical anatomy and surgical flap site identification for donor tissue. In such a scenario, the foundation model is guided towards an accurate recommendation since the vast amounts of data provided as inputs to the model outline best practices made by actual seasoned medical professionals. Additionally, the detection data and annotation data may optionally be assisted by a human operator that is trained in such practices, to better focus the attention of the foundation model on the appropriate regions to consider for donor sites based on the desired treatment criteria 160 for an upcoming medical procedure.

An example medical history of a patient may include the history of prior medical procedures attempted on the patient, along with documented notes from medical professionals on the successes and failures of the prior medical procedures. Examples of prior medical images of the patient that may be considered by the foundation model 140, which may include, but are not limited to, photographic images, x-rays scans, CT (computer tomography) scans, MRI (magnetic resonance imaging) scans, ultrasound scans, PET (positron-emission tomography) scans, SPECT (single-photon emission computer tomography) scans, mammography scans, sonography scans, to name a few. The prior medical history with prior medical images may be considered by the foundation model 140, together with the newly captured 3D images with volumetric data. Additional context data 170 may also be considered by the foundation model, which may include, but is not limited to, any variety of medical data such as: treatises on human anatomy, medical guides for surgical flap procedures, as well as medical images and/or annotated medical images of numerous prior successful medical procedures with similar characteristics.

The format of the output 150 provided by the AI based recommendation system 100 may be text based, visual image based, or combinations thereof. For example, a flap recommendation (e.g., flap site, size, placement, tissue, etc.) may be provided as AI generated text output or AI generated visual image output (e.g., a 3D image), or combinations thereof. An example AI generated text output might include detailed recommendations for harvesting a donor flap, with a description of a location and size of a flap to be harvested, as well as any additional details about the tissue itself (e.g., tissue details) with harvesting requirements (e.g., depth and volume of the donor flap to be extracted, include extraction of support tissue such as blood vessels, supporting bone, fat, nerves, tendons, ligaments, etc.). Another example AI generated text output w might describe detailed recommendations for flap placement, with a description of location, size and, orientation for placement of the donor flap, along with details for connection of the donor flap in the treatment site (e.g., depth and volume of the pocket to be created, connect support issues such as blood vessels, or ligaments, tendons, etc.). In another example, an AI generated visual image output may include a 3D image, where the 3D image may be annotated or marked (e.g., with graphical indicators, fill codes, color, text, etc.) to clearly identify a donor flap site, size, and tissue details for harvesting. In still another example, an AI generated visual image output may include a 3D image, where the 3D image may be annotated or marked (e.g., with graphical indicators, fill codes, color, text, etc.) to clearly identify flap placement at a treatment site.

It is expected that excellent benefits may be achieved by the described foundation model methods. For example, a less experienced medical professionals may use the foundation model based AI recommendation system as a training or learning tool to be educated on best surgical practices. Additionally, the medical professionals are enabled to make quicker and more informed decisions, leading to reduced errors and reduced cost of medical services. Accuracy of diagnoses is improved, and potential health risks may be assessed and predicted. Personalized treatment plans may be quickly formulated, providing better care and improved patient satisfaction with better patient outcomes and reduced risks of complications.

Although shown as individual components 110-150, these are merely functional partitions and may be combined or eliminated in specific implementations as may be desired.

FIG. 2 illustrates a detailed portion of another example AI based recommendation system 200 that is capable of implementing aspects of the techniques and technologies presented herein. As illustrated the example system 200 includes an input component 110 with functional blocks for image capture 112, a three-dimensional (3D) model 114, and image data 116. Further illustrated is a plurality (N) of image capture devices (Device$_1$ to Device$_N$, N=9) or image sensors, which are positioned in a 3D space about a patient 201.

Each of the image capture devices may be positioned at a different physical location and with a different observation angle relative to the patient 201. For example, a first device (Device$_1$) may be posited to capture images of the front face of the patient 201, while another device (e.g., Device$_5$) may be positioned to capture images from a top-down view of the patient, and a third device (e.g., Device$_6$) may positioned to capture images from a back view of the patient. Each of the image capture devices (Device$_1$ to Device$_N$) may thus be positioned to capture different angles, orientations, faces and/or surfaces of the patient 201.

Operationally, the input component 110 is configured to capture a plurality of images (e.g., Image$_1$ to Image$_N$) of patient 201 in the form of image data 116, which are applied to the 3D model 114 to also result in additional images data that that include volumetric data as will be further described herein. Thus, the system 100 is configured to capture a plurality of images (e.g., image data 116) of the patient and form 3D image data 116 by applying at least a portion of a plurality of images to the 3D model 114. The image data 116 in various examples may be captured from various image sensors or image capture devices such as digital cameras, digital video, analog cameras, analog video, and the like, which are oriented in a 3D space about the patient to capture a variety of fields of view and angles, as may be required to achieve proper imaging for the 3D model.

Meta data may also be captured along with the images as shown in FIG. 2. The meta data may include additional information, such as may be used by the 3D model. For example, meta data may include depth information related to each of the individual images that are captured, where the 3D model may combine (e.g., "fuse") the images based at least in part on the related meta data that is captured along with the images. Additional meta data that may be captured from the image sensors may include sensor identification (e.g., serial number, product ID, model ID, etc.), as well as various settings for the image sensor (e.g., color or intensity settings, illumination or ambient levels, resolution, etc.).

In some examples, the image data 116 may correspond to RGB-D data, where RGB-D data corresponds to Red, Green, Blue plus Depth. In various examples, RGB-D data may be generated by a newly available inexpensive depth camera, such as a Microsoft Kinect camera, which provides per-pixel depth information aligned with the image pixels. In other examples, RGB-D data may be generated using a stereo camera setup. The various images with RGB-D data may be combined using a fusion process, which may form the 3D image data 116 discussed herein. The captured data from the RGB-D type camera devices may thus be "fused" together, yielding enhanced accuracy of depth in the resulting 3D images. Fusion may employ alignment of image data in forming the 3D images. For example, depth, color, and/or intensity of pixels may be used as part of the alignment process. In some examples, the image capture devices may be able to also capture infra-red image data, which may further enable enhanced 3D image formation with improved accuracy.

Figure 3:
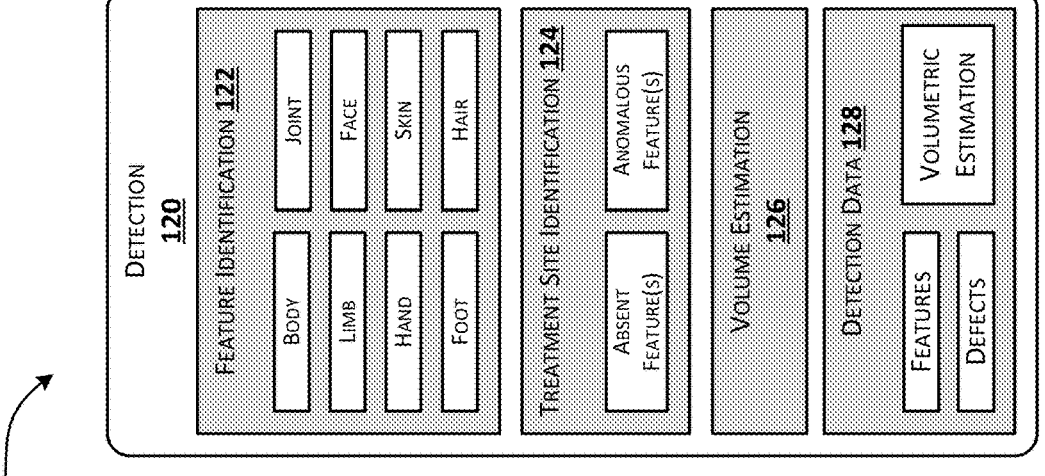
FIG. 3 illustrates another detailed portion of an example AI based recommendation system that is capable of implementing aspects of the techniques and technologies presented herein.

FIG. 3 illustrates another detailed portion of an example AI based recommendation system 300 that is capable of implementing aspects of the techniques and technologies presented herein. As illustrated the example system 300 includes functional blocks for feature identification 122, defect identification 124, volume estimation 126, and detection data 128. Operationally, the detection component 120 may be configured to evaluate the various captured images 116 of the patient, either with or without human assistance. From the image data 116, feature identification 122 of the patient may be performed. As shown in FIG. 3, feature identification may include identification and/or labeling of various body parts, including at least body sections, limb, hand, foot, joint, face, skin, and hair. Also as shown in FIG. 3, defect identification 124 may include identification of one or more absent features, and/or identification of one or more anomalous features. An absent feature may refer to a missing or absent body part that may result from a congenital condition, trauma, amputation, or removal; while an anomalous feature may be a result of trauma, disfigurement, or a disease such as cancer, etc. Found features may be compared or mapped to a 3D anatomical model so that the detection component 120 may identify defects, either with or without human assistance.

Patient 301 is also shown in FIG. 3 for context, with examples body features such as head 310 and torso 330, shoulders 322, upper arms 341, elbows 323, forearms 342, hands 340 and feet 350. Also shown are example facial features on the head 310, including hair 314m brow 315, forehead 311, upper lip 312, chin 313, cheek 316, ear 317 and neck 318. These example features may be used to construct a 3D wire frame representation (e.g., a 3D model) of the patient, as shown by the graphical overlays of FIG. 3.

Figure 4:
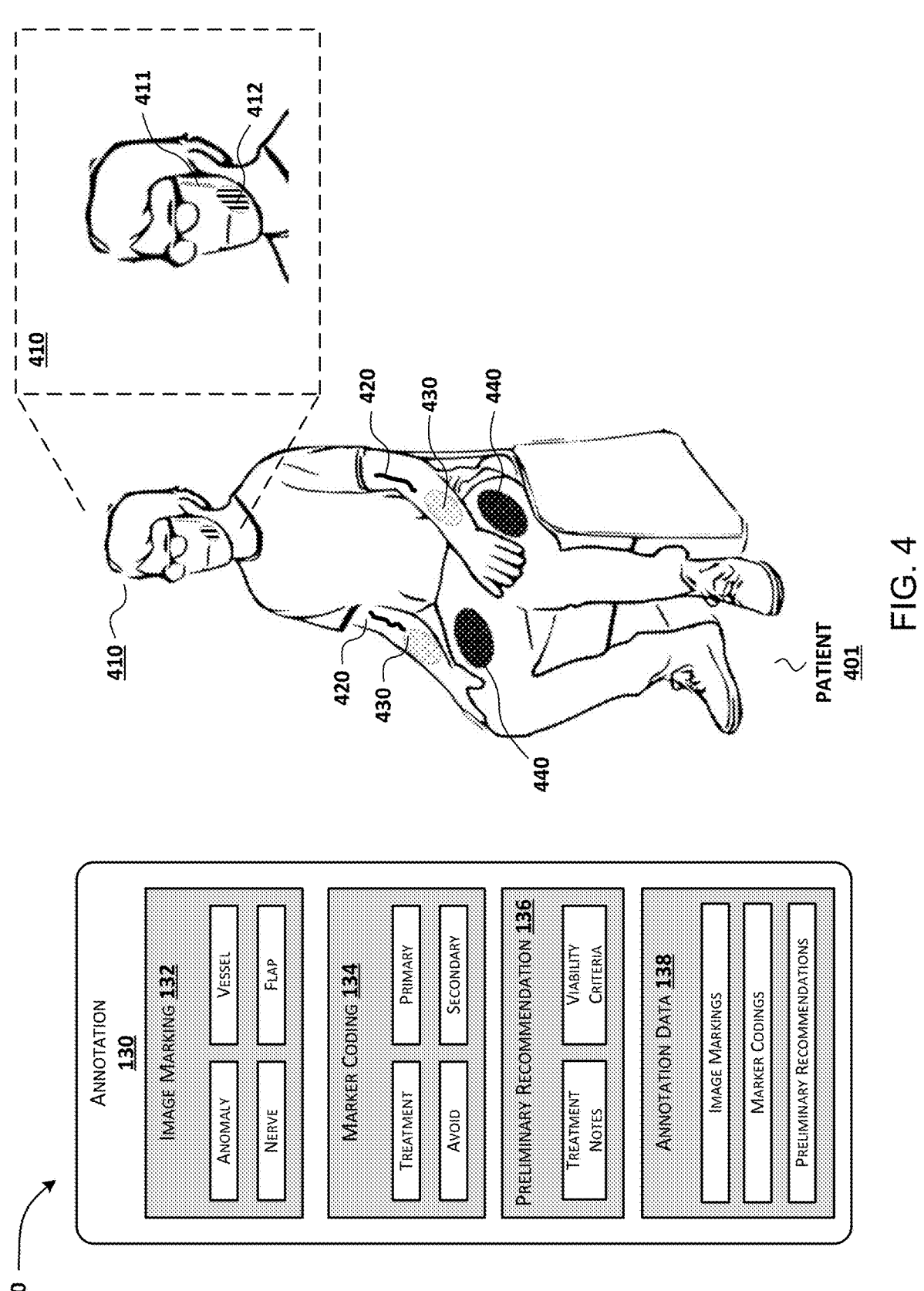
FIG. 4 illustrates yet another detailed portion of an example AI based recommendation system that is capable of implementing aspects of the techniques and technologies presented herein.

FIG. 4 illustrates yet another detailed portion of an example AI based recommendation system 400 that is capable of implementing aspects of the techniques and technologies presented herein. As illustrated the example system 400 includes an annotation component 130 with functional blocks for image marking 132, marker coding 134, preliminary recommendation 136, and annotation data 138. Operationally, the annotation component 140 is configured to evaluate the various captured images 116 of the patient and any additional detection data 128, either with or without human assistance; as previously described. For FIG. 4, the annotation component 130 shows additional detailed blocks for image making 132 to include specific designations for an anomaly (or treatment site), a vessel, a nerve and/or a flap (donor site). Also, additional detailed blocks are included for maker coding 134 to include specific designations for treatment area, avoidance area, primary donor site, and secondary donor site.

FIG. 4 further illustrates an image of a patient 401 with image overlays to illustrate markings that are coded with specific color or fill codes in accordance with embodiments described herein. As shown, the image of patient 401 has a head 410 with an image marking for a blood vessel 411 and a treatment area 412. The image of patient 401 further includes an image marking for blood vessels 420 in the upper arms and first set of possible primary donor sites 430 in a region of the forearms. Also, a set of secondary donor sites 440 are illustrated along a surface of the thighs of the patient 401. Each of the specific features are illustrated as having different marking codes (e.g., colors and/or fill codes) to illustrate an example marking scheme: one code for treatment area, another code for avoidance, still another code for primary donor site, yet another code for secondary donor site, etc. In addition to the marked images being coded to represent a type of preliminary recommendation, addition annotation data 138 may be included for text based recommendations that are intended to address recommendations for the treatment criteria 160 as previously described.

Figure 5:
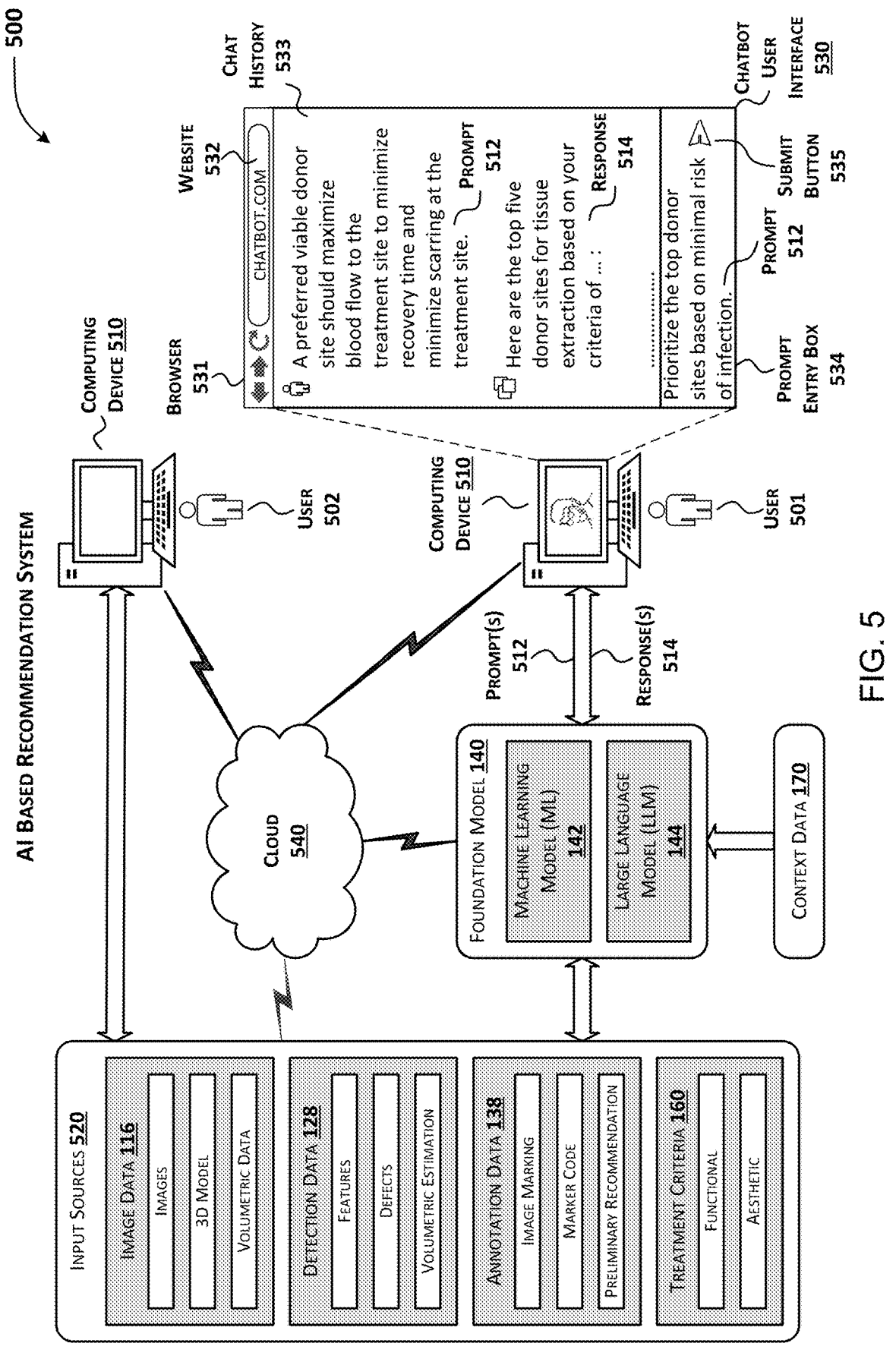
FIG. 5 illustrates still another example AI based recommendation system that is capable of implementing aspects of the techniques and technologies presented herein.

FIG. 5 illustrates still another example AI based recommendation system 500 that is capable of implementing aspects of the techniques and technologies presented herein. As illustrated, AI based recommendation system 500 includes first and second computing devices 510, input sources 520, a chatbot user interface 530, a computing cloud 540, a foundation model 140, and context data 170. Human operators of the first and second computing devices 510 are also illustrated, as shown by users 501 and 502, respectively.

System 500 operates in a similar manner as system 100 as previously described with respect to one or more of FIGS. 1-4. However, for the example of FIG. 5, a detailed example interaction of a chatbot interface is included to demonstrate additional examples where one or more human operators may interact with the foundation model 140 during one more of the steps for input, detection, annotation, and recommendation.

For some examples described herein, the foundation model 140 may be separated from or part of a cloud computing environment (e.g., cloud 140). For some additional examples described herein, the foundation model 140 may be separated from or part of one or more of the computing devices 510.

The input sources 520 to the foundation model 140 are illustrated as including image data 116, detection data 128, annotation data 138, and a treatment criteria 160. The image data 116 may include images, 3D models, meta data and volumetric data associated with a patient; while the detection data 128 may include features, defects, and volumetric estimation of one or more sites of the patient; and annotation data 138 may include image marking, marker coding, and preliminary recommendations, all as previously described herein. The treatment criteria 160 may include functional and aesthetic objectives, or combinations thereof as previously described.

Context data 170 may also serves as another data source for the foundation model 140. However, context data 170 may be used to fine tune the foundation model for a medical context, seed prompts to the foundation model for a medical context, or otherwise be used to tailor attention of the foundation model 140 for the intended purposes described herein. The context data may include any number of medical references that are text based, image based, or combinations thereof. Thus, the context data may include medical books, treatises, articles, studies, publications, and the like. For example, one or more references may be provided for medical anatomy, plastic surgery, reconstruction surgery, functional tissue selection, aesthetic tissue selection, defect identification, donor flap identification, donor flap extraction, as well as any reference images related to the same.

As depicted in FIG. 5, the foundation model 140 may include a machine learning model (ML) 142 and/or a large language model (LLM) 144. A first human operator (e.g., USER 501) may interact with the foundation model 140 via the first computing device 510, either directly or through a cloud 540 based resource, or via some other network connectivity. The first human operator may be a medical professional (e.g., a doctor, nurse, technician, healthcare assistant, etc.) that interfaces with the foundation model 140 to participate or initiate one or more functional procedures such as image capture, detection, annotation, recommendation, or treatment criteria. Similarly, a second human operator, which may be remotely located with respect to the first human operator, may be in a consulting role to participate or initiate a portion of the one or more of the functional procedures.

A user (e.g., 501 or 502) may operate a computing device 510 to navigate a browser 531 to a chatbot website 532. Chatbot website 532 is one non-limiting example of an application program that may utilize a natural language model (NLM) interface to interact with users in a human-like way. The Foundation model 140 used by the chatbot website 532 may be located on a remote computing device, although it may alternatively be implemented by computing device 510. In other examples, the chatbot website 532 may be implemented on a local or secured network that is inaccessible to the public (e.g., behind a firewall with secured access), such as might be used for a proprietary implementation on a secured platform. In still other examples, the chatbot website 532 implementation may be replaced with an application program that is run directly on computing device 510, which may also be in a secured environment.

A chatbot user interface 530 used by the chatbot website 532, in this example, may include a prompt entry box 534 for a user to enter a prompt 512. Clicking or otherwise selecting a trigger associated with a submit button 535 on the chatbot user interface 530 will result in prompt 512 being submitted to the foundation model 140 that is used by the chatbot website 532. Chatbot user interface 530 may also include a history 533 of prior submitted prompts 512 and any prior results or responses 514 received from the foundation model 140 responsive to a prior submitted prompt 512. In some instances, after a prompt 512 is submitted to the chatbot user interface 530, an icon or graphic element may be shown (e.g., blinking ellipses, an hourglass, spinning wheel, etc.) in the chat history area 533 of the display to indicate that the submitted prompt is under review such as when a prompt is processed by the foundation model 140.

After a user prompt 512 is submitted to the foundation model 140 via the chatbot user interface 530, the foundation model 140 processes the prompt to capture the semantic meaning of the words or phrases in the prompt so that the information is in a form to be processed by the LLM 144. This process may be achieved by leveraging the embedding representations obtained by running a natural language understanding model that annotates different components of the user prompt. The embedding vectors can then be used as input features for various NLP tasks by the LLM, such as sentiment analysis or text classification, or other meaningful insights from the text data.

The foundation model 140 may use various natural language processing (NLP) techniques to determine context around keywords and phrases in the text data. One technique, called contextual word embeddings, represents each word found in a text prompt as a dense, low-dimensional vector that captures meaning in the context of the surrounding words by applying deep learning models. The LLM 144 in the present system 500 can be trained (e.g., via a machine learning model 142) on large amounts of text data to learn the patterns and relationships between words and phrases in different contexts. When processing a piece of text data, words and phrases can be context related to their closely related target keyword or phrase in their embeddings by the LLM 144.

Although the above description illustrates a text based user interface, this is merely one non-limiting example, and the specific implementation of the user interface may be text based, visual or graphically based, audio or voice based, or any combination thereof, without departing from the spirit of the present disclosure. Thus, the format of the prompts 512 submitted and received by the foundation model 140, and the format of the recommendations or responses(s) 514 provided as output by foundation model 140 may include: text based (e.g., written), visual based (e.g., images), or audio based (e.g., spoken) recommendations via computing device 510. In one example, the user 501 may mark images to submit as a prompt 512 to the foundation model 140 via a graphical user interface. In another example, foundation model 140 may mark images to provide as a response 514 to be displayed by computing device 510 as visual images of the patient in a 3D model, with the annotations visible on the 3D model. In still another example, the user 501 may submit spoken prompts 512 to the foundation model 140 by a microphone based input via computing device 510. In yet another example, the foundation model 140 may generate a spoken response 514 that the user 501 may hear from a speaker or other audio output of computing device 510.

AI assisted interactions with human operators are contemplated by the AI based recommendation system 500 of FIG. 5. Below are some non-limiting examples of interactions.

In a first example, a human operator 501 may interface with the foundation model 140 via a prompt 512 to initiate the scanning of a patient based on a specific treatment criteria 160. In this example, the AI system 500 may process the treatment criteria and provide a detailed instruction to the human operator as a response 514, instructing the human operator 501 to position the patient in an appropriate location and orientation relative to one or more image capture devices to initiate an image scan to form a 3D model of the patient with volumetric data.

In a second example, a second human operator 502 may interface with the foundation model 140 via a prompt 512 to initiate detection and/or marking of features, treatment sites, defects, and/or recommendations related to a patients treatment area. In this example, the human operator may be specially trained (e.g., a specially trained technician, doctor, healthcare worker, assistant, etc.) on identification of defects and anomalies for the specific treatment criteria (e.g., tumor removal). The human operator may be presented with images and a user interface to graphically mark the patient's images with the specific feature area or treatment site (i.e., the defect zone or area) on the patient, as well as any preliminary recommendations for flap harvesting, and avoidance regions or zones for the patient.

In a third example, the foundation model 140 may generate an initial recommendation for flap harvesting based on a previously submitted treatment criteria 160, patient images data 116, that were previously processed for detection, annotation, and the like. In this example, a human operator 501 may review the results or responses 514 in the chatbot interface 530, and make further refinements to the recommendation via additional prompts 512. For example, in a first chatbot session, the foundation model 140 may generate an output recommendation that relates to a treatment criteria to "maximize blood flow to the treatment site to minimize recovery time and minimize scarring at the treatment site." After further review by the human operator, the treatment criteria may be modified by submitting a prompt 512 to "prioritize, the top donor sites based on minimal risk of infection." In this manner, the AI based recommendation system serves as an analysis tool that works under the supervision of human operators to increase productivity, reduce errors, and refine medical procedures to optimize flap harvesting procedures as needed in a dynamic environment.

The above described technique, features, and methods may be implemented in multiple ways, including the flow charted illustrations of FIGS. 6-9 described below, which are considered non-limiting examples.

FIG. 6 illustrates is an example flow diagram 600 for aspects of an AI based recommendation system, in accordance with various aspects described herein. The flow diagram 600 includes blocks 610, 620, 630, 640, 650, 660 and 670; which together provide a working example of systems 100 to 500 such as discussed previously with respect to FIGS. 1 to 5. Processing for the various blocks of flow diagram 600, which may be described as processes, methods, steps, or functions, may commence at block 610.

At block 610, "Input Prompts and 3D Image Data Including Volumetric Data", system inputs are captured. The system inputs may include input prompts such as patient records or treatment criteria as well as 3D image data associated with a patient, such as data 116, which includes volumetric data. Processing continues from block 610 to block 620.

At block 620, "Receive Input Prompts and 3D Image Data including Volumetric Data", the system inputs from block 610 are received by the AI based recommendation system (e.g., systems 100 to 500). Thus, block 620 also corresponds to receiving 3D image data associated with a patient (e.g., image data 116), where the 3D image data includes volumetric data. Processing continues from block 620 to block 630.

At block 630, "Detect Treatment Site(s) based on Received Input Prompts and 3D Image Data", treatment sites are detected based on the received input prompts (e.g., treatment criteria) and the 3D image data (e.g., image data 116). The treatment sites may correspond to features and defective anatomical sites, such as may be considered for aesthetic and/or functional objectives; which may be identified by detection data 128. Thus, block 630 also corresponds to detecting one or more defective anatomical sites associated with the patient based on the received three-dimensional (3D) image data. Processing continues from block 630 to block 640.

At block 640, "Annotate the 3D image data with Detected Treatment site(s) and Preliminary Donor Site Recommendations", the 3D image data (e.g., image data 116) and the detected treatment (e.g., detection data 128) associated with the patient are annotated (e.g., annotation data 138) for possible donor site recommendations. Thus, block 640 also corresponds to annotating the three-dimensional (3D) image data with one or more of the detected defective anatomical sites associated with the patient. Processing continues from block 640 to block 650.

At block 650, "Identify and Recommend Viable Donor Sites with a Foundation Model based on Input Prompts and the Annotated 3D Image Data", viable donor sites are identified by the foundation model (e.g., foundation model 140) for flap harvesting based on the treatment criteria (e.g., treatment criteria 160) and the annotated 3D image data (e.g., annotation data 138). Thus, block 650 also corresponds to evaluating the annotated three-dimensional (3D) image data with a foundation model to identify viable sites for flap harvesting based on a criteria for care or treatment of the patient. Processing continues from block 650 to block 660.

At block 660 "Check for additional inputs?", the AI based recommendation system determines if additional inputs are entered by a human operator. When additional inputs are entered by a human operator (e.g., additional prompts 512), processing continues from block 660 to block 620. When no additional inputs are entered by a human operator, processing may continue from block 660 to block 670.

At block 670 "Output Recommendations", the system outputs are output to the user (e.g., via a chatbot user interface 530). Thus, block 670 also corresponds to providing a recommendation of one or more viable sites for flap harvesting associated with care or treatment of the patient.

The processes illustrated in FIG. 6 demonstrate an iterative process that is guided by a human operator for an AI based recommendation system. As illustrated, additional prompts can be provided to the AI based recommendation system to tune or adapt the outputs to are more suitable solution than the originally recommended flap harvesting procedures. Further refinements are also possible, where highly skilled medical experts may guide the AI based recommendation system to tune performance and optimize the recommendation for a given patient.

FIG. 7 illustrates is a detailed portion of a flow diagram 700 for aspects of an AI based recommendation system, in accordance with various aspects described herein. The flow diagram 700 includes details of blocks 610 and 620, which are generally as discussed previously with respect to FIGS. 1 to 6. Processing for the various blocks of flow diagram 700, which may be described as processes, methods, steps, or functions, may commence at block 610.

Block 610 of FIG. 7, "Input Prompts", is substantially similar to block 610 of FIG. 6, with additional detailed blocks contained therein as block 612, 614, and 616. At block 612, "Select treatment Criteria", a treatment criteria may be selected. Block 612 is followed by block 614, "Collect Patient Medical Records", where patient medical records are collected from any available sources. Patient medical records may include patient information such as medical records or reports of prior medical procedures, doctors notes, and/or medical images, which may be any form of medical images as previously described. Block 614 may be followed by block 616, "Capture Images of Patient with Volumetric Data", where 3D image data (e.g., image data 116) including volumetric data may be captured such as via a collection of image sensors as previously discussed. Processing continues from block 616 to block 620.

Block 620 of FIG. 7, "Receive Inputs", is substantially similar to block 620 of FIG. 6, with additional detailed blocks contained therein as block 622 and 624. At block 622, "Provide Input Prompts to Foundation Model with 3D Images and Volumetric Data", input prompts and/or 3D images with volumetric data (e.g., image data 116) may be provided to the foundation model (e.g., foundation model 140). Similarly, at block 624, "Provide Input Prompts to Medical Professional with 3D Images and Volumetric Data", input prompts and/or 3D images with volumetric data (e.g., image data 116) may be provided to a human operator (e.g., user 501). Block 622 and 624 may be operated in parallel, and followed by block 630 as previously described.

Figure 8:
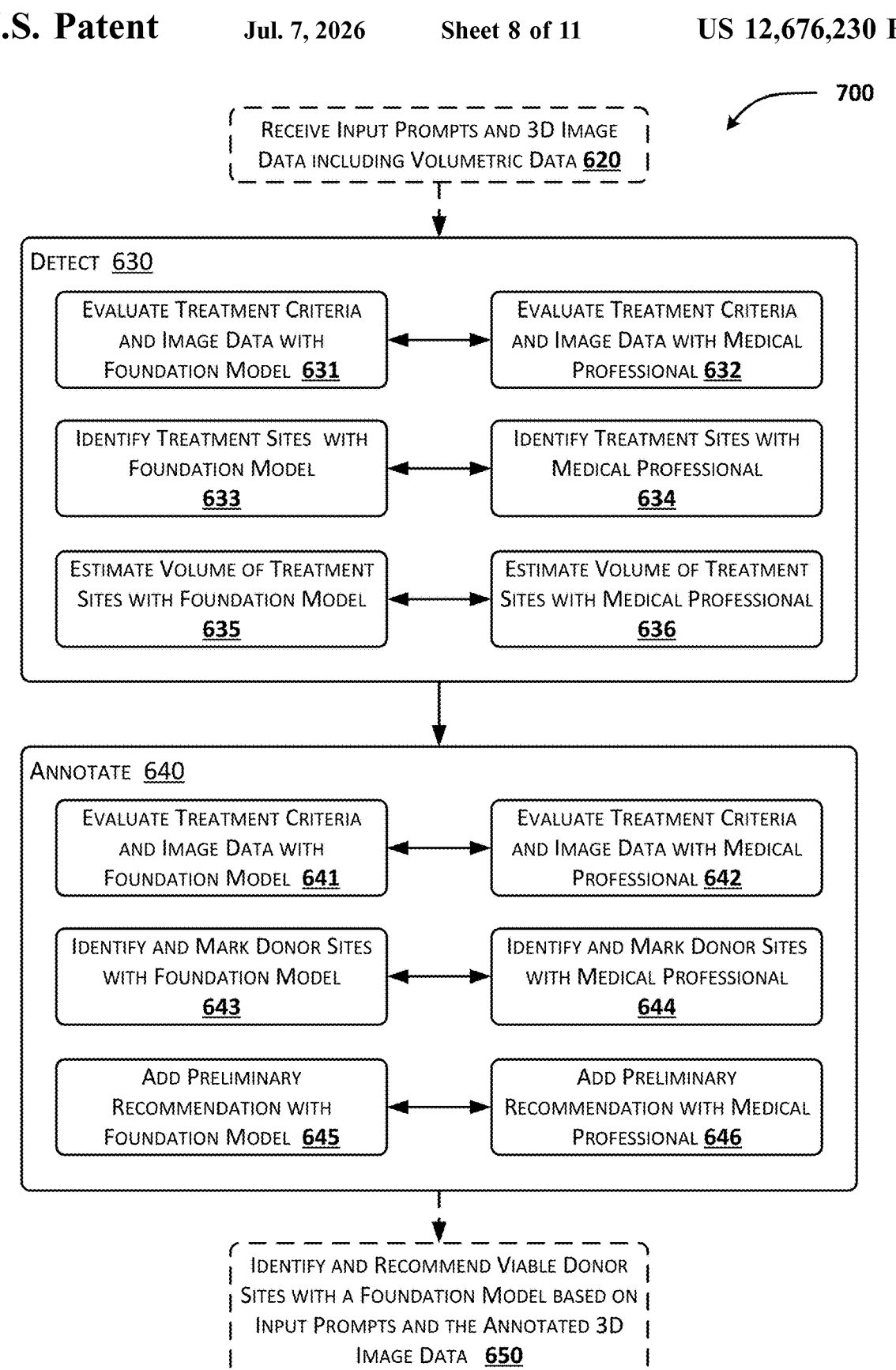
FIG. 8 illustrates is another detailed portion of a flow diagram for aspects of an AI based recommendation system, in accordance with various aspects described herein.

FIG. 8 illustrates is another detailed portion of a flow diagram 800 for aspects of an AI based recommendation system, in accordance with various aspects described herein. The flow diagram 800 includes details of blocks 630 and 640, which are generally as discussed previously with respect to FIGS. 1 to 6. Processing for the various blocks of flow diagram 800, which may be described as processes, methods, steps, or functions, may commence at block 630.

Block 630 of FIG. 8, "Detect", is substantially similar to block 630 of FIG. 6, with additional detailed blocks contained therein as blocks 631, 632, 633, 634, 635, and 636. Blocks 631, 633 and 635 correspond to a Foundation Model approach, while block 632, 634 and 636 correspond to a medical professional approach. Additionally, collaboration between the foundation model and the medical professional is contemplated as illustrated in FIG. 8

At block 631, "Evaluate Treatment Criteria and Image Data with Foundation Model", a treatment criteria (e.g., 160) is evaluated by the foundation model (e.g., 140); while at block 632, "Evaluate Treatment Criteria and Image Data with Medical Professional", the treatment criteria (e.g., 160) is evaluated by the medical professional. In some instances, the treatment criteria may be collaboratively evaluated by the medical professional (e.g., a human operator) with assistance from the foundation model. In some examples, block 631 or 632 may be followed by block 633, while in other examples block 631 or 632 may be followed by block 634; and in still other examples block 631 or 632 may be followed by both blocks 633 and 634.

At block 633, "Identify Treatment Sites with Foundation Model", a treatment site may be identified in the image data (e.g., 116) by the foundation model (e.g., 140); while at block 633, "Identify Treatment Sites with Medical Professional", the treatment site may be identified by the medical professional. In some instances, the treatment site may be collaboratively identified by the medical professional (e.g., a human operator) with assistance from the foundation model. In some examples, block 633 or 634 may be followed by block 635, while in other examples block 633 or 634 may be followed by block 636; and in still other examples block 633 or 634 may be followed by both blocks 635 and 636.

At block 635, "Estimate Volume of Treatment Sites with Foundation Model", a volume of a treatment site(s) may be estimated by the foundation model (e.g., 140); while at block 636, "Estimate Volume of Treatment Sites with Medical Professional", the volume of the treatment site(s) may be evaluated by the medical professional. In some instances, the volume of the treatment site(s) may be collaboratively estimated by the medical professional (e.g., a human operator) with assistance from the foundation model. Block 635 or 636 may be followed by block 640.

Block 640 of FIG. 8, "Annotate", is substantially similar to block 640 of FIG. 6, with additional detailed blocks contained therein as blocks 641, 642, 643, 644, 645, and 646. Blocks 641, 643 and 645 correspond to a Foundation Model approach, while block 642, 644 and 646 correspond to a medical professional approach. Additionally, collaboration between the foundation model and the medical professional is contemplated as illustrated in FIG. 8

At block 641, "Evaluate Treatment Criteria and Image Data with Foundation Model", a treatment criteria (e.g.,

160) and image data (e.g., 116) is evaluated by the foundation model (e.g., 140); while at block 642, "Evaluate Treatment Criteria and Image Data with Medical Professional", a treatment criteria (e.g., 160) and image data (e.g., 116) is evaluated by the medical professional. In some instances, the treatment criteria and image data may be collaboratively evaluated by the medical professional (e.g., a human operator) with assistance from the foundation model. In some examples, block 641 or 642 may be followed by block 643, while in other examples block 641 or 642 may be followed by block 644; and in still other examples block 641 or 642 may be followed by both blocks 643 and 644.

At block 643, "Identify and Mark Donor Sites with Foundation Model", donor sites for extraction are identified and marked on the images of the patient by the foundation model (e.g., 140); while at block 644, "Identify and Mark Donor Sites with Medical Professional", donor sites for extraction are identified and marked on the images of the patient by the medical professional. In some instances, donor sites for extraction are collaboratively identified and marked by the medical professional (e.g., a human operator) with assistance from the foundation model. In some examples, block 641 or 642 may be followed by block 643, while in other examples block 641 or 642 may be followed by block 644; and in still other examples block 641 or 642 may be followed by both blocks 643 and 644.

At block 645, "Add Preliminary Recommendation with Foundation Model", a preliminary recommendation (e.g., text, mark coding, etc.) for extraction of tissue are identified and annotated on the images of the patient by the foundation model (e.g., 140); while at block 646, "Add Preliminary Recommendation with Medical Professional", preliminary recommendation (e.g., text, mark coding, etc.) for extraction of tissue are identified and annotated on the images of the patient by the medical professional. In some instances, preliminary recommendations for extraction of tissue are collaboratively identified and annotated by the medical professional (e.g., a human operator) with assistance from the foundation model. Blocks 645 or 646 may be followed block 650.

Figure 9:
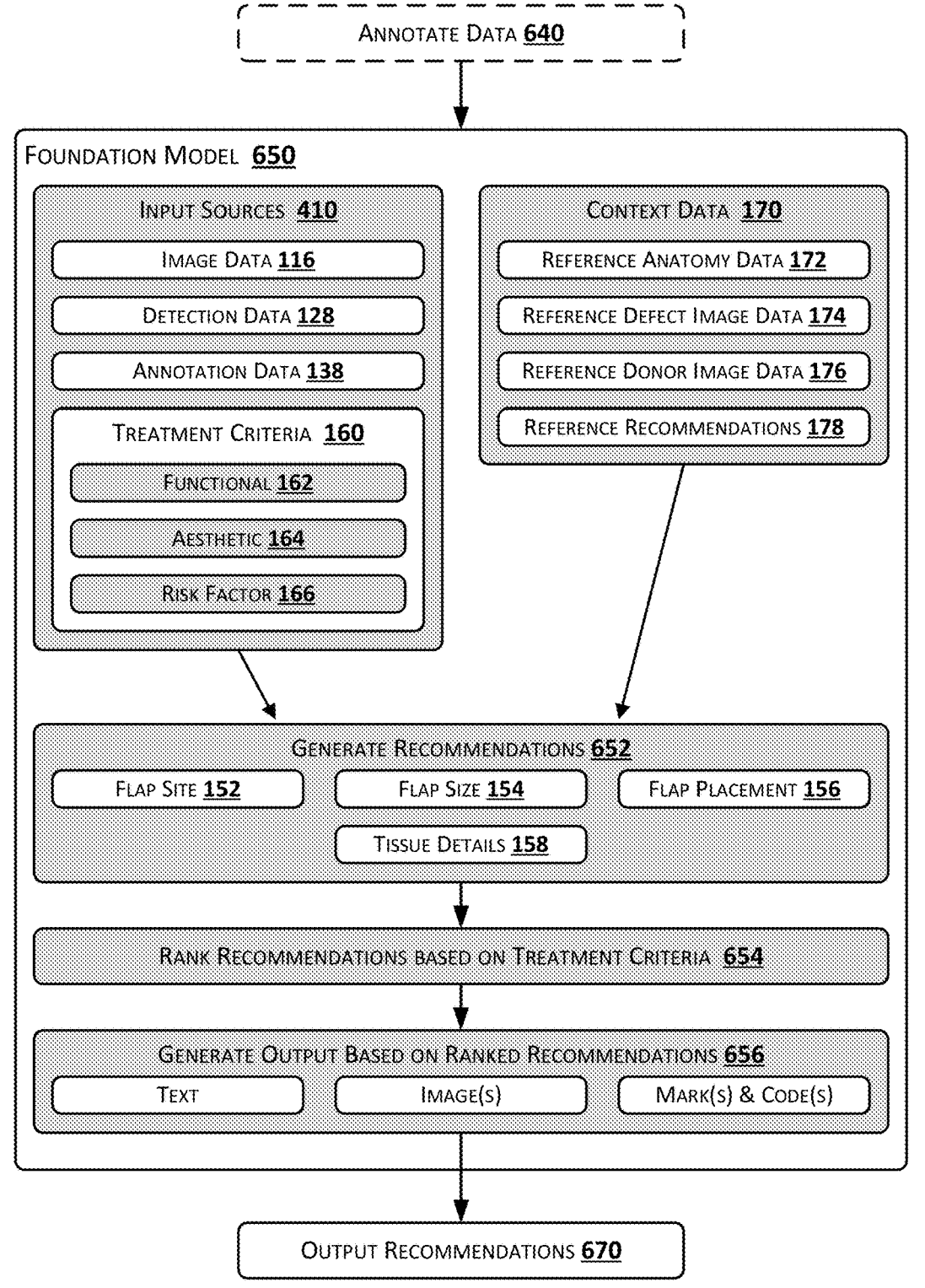
FIG. 9 illustrates is yet another detailed portion of a flow diagram for aspects of an AI based recommendation system, in accordance with various aspects described herein.

FIG. 9 illustrates is yet another detailed portion of a flow diagram 900 for aspects of an AI based recommendation system, in accordance with various aspects described herein. The flow diagram 900 includes details of blocks 650, which are generally as discussed previously with respect to FIGS. 1 to 6. Processing for the various blocks of flow diagram 900, which may be described as processes, methods, steps, or functions, may commence at block 650.

Block 650 of FIG. 9, "Foundation Model", is substantially similar to block 650 of FIG. 6, with additional detailed blocks contained therein as blocks 652, 654, and 656. Additionally, input sources 410 and context data 170 are illustrated to show all sources of information that are leveraged by the foundation model in generating recommendations. As shown, Input sources 410 may include image data 116, detection data 128, annotation data 138 and treatment criteria 160. Treatment criteria 160 may further include functional objectives 162, aesthetic objectives 164, and risk factor objectives 166. Context data 170 further includes reference anatomy data 172, reference defect image data 174, reference donor image data 176, and reference recommendations 178.

At Block 652, "Generate Recommendations" the foundation model (e.g., 140) determines a recommendation in consideration of all input sources and context data (e.g., presented via prompts, tuning, or combinations thereof), including recommendations for flap site 152, flap size 154, flap placement 156, and tissue detail(s) 158. Block 652 is followed by block 654, "Rank Recommendations based on Treatment Criteria", where the recommendations for harvesting donor flap sites are ranked according to the treatment criteria (e.g., 160) as specified. Block 654 is followed by block 656, "Generate Output Based on Ranked Recommendations", wherein the output is generated by the foundation model, which may be used to generate text, images, audio, or combinations thereof. Block 656 may be followed by block 670.

The particular implementation of the technologies disclosed herein is a matter of choice dependent on the performance and other requirements of a computing device. Accordingly, the logical operations described herein are referred to variously as states, operations, structural devices, acts, modules, or components. These states, operations, structural devices, acts, modules, or components can be implemented in hardware, software, firmware, in special-purpose digital logic, and any combination thereof. It should be appreciated that more or fewer operations can be performed than shown in the figures and described herein. These operations can also be performed in a different order than those described herein.

It also should be understood that the illustrated methods can end at any time and need not be performed in their entireties. Some or all operations of the methods, and/or substantially equivalent operations, can be performed by execution of computer-readable instructions included on a computer-storage media, as defined below. The term "computer-readable instructions," and variants thereof, as used in the description and claims, is used expansively herein to include routines, applications, application modules, program modules, programs, components, data structures, algorithms, and the like. Computer-readable instructions can be implemented on various system configurations, including single-processor or multiprocessor systems, minicomputers, mainframe computers, personal computers, hand-held computing devices, microprocessor-based, programmable consumer electronics, combinations thereof, and the like.

Thus, it should be appreciated that the logical operations described herein are implemented (1) as a sequence of computer implemented acts or program modules running on a computing system and/or (2) as interconnected machine logic circuits or circuit modules within the computing system. The implementation is a matter of choice dependent on the performance and other requirements of the computing system. Accordingly, the logical operations described herein are referred to variously as states, operations, structural devices, acts, or modules. These operations, structural devices, acts, and modules may be implemented in software, in firmware, in special purpose digital logic, and any combination thereof.

Figure 10:
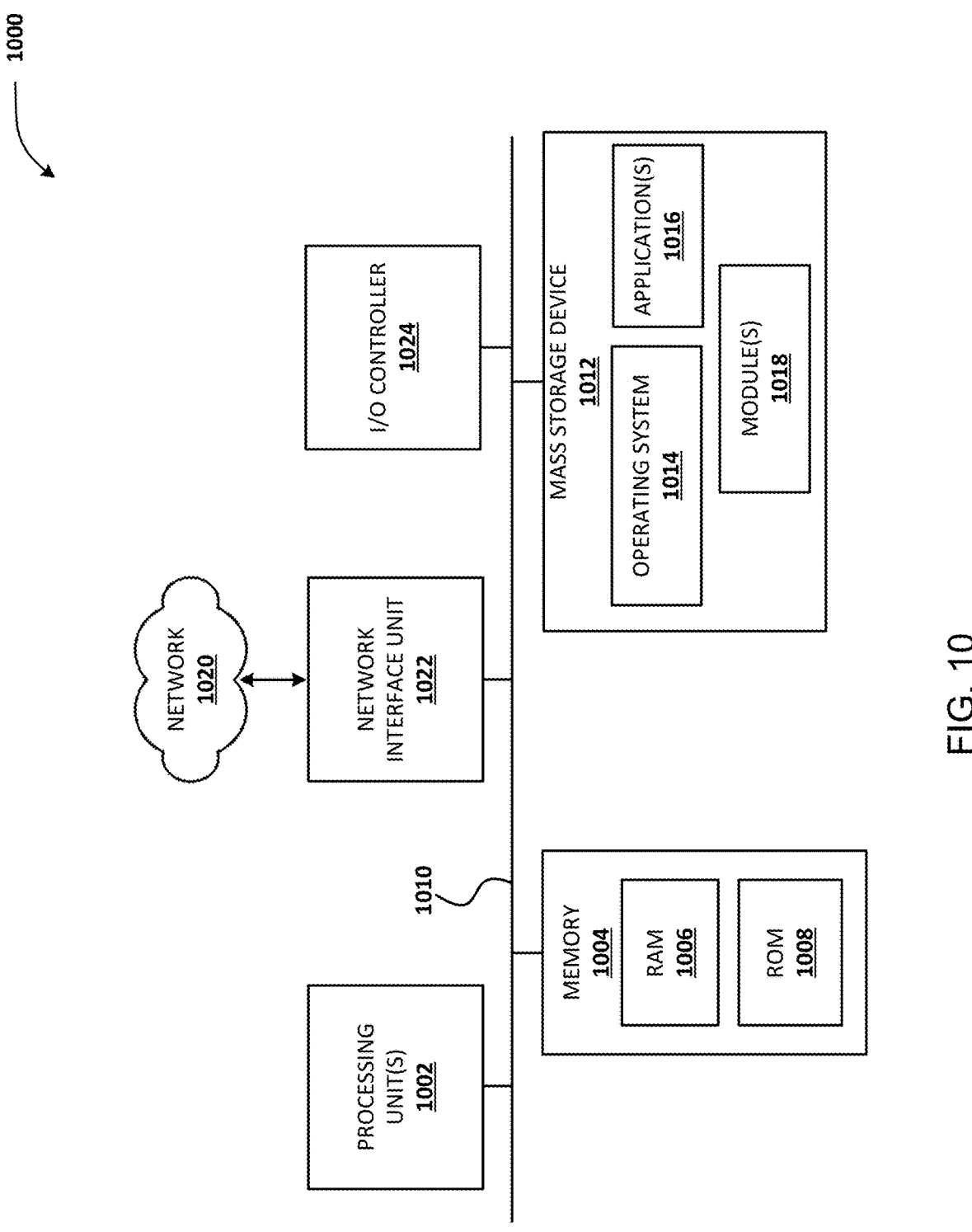
FIG. 10 is a computer architecture diagram illustrating an illustrative computer hardware and software architecture for a computing system capable of implementing aspects of the techniques and technologies presented herein.

FIG. 10 shows additional details of an example computer architecture 1000 for a device, such as a computer or a server configured as part of the systems described herein (e.g., 100, 200, etc.), capable of executing computer instructions (e.g., a module or a program component described herein). The computer architecture 1000 illustrated in FIG. 10 includes one or more processing unit(s) 1002, a system memory 1004, including a random-access memory 1006 ("RAM") and a read-only memory ("ROM") 1008, and a system bus 1010 that couples the memory 1004 to the processing unit(s) 1002.

Processing unit(s) or processor(s), such as processing unit(s) 1002, can represent, for example, a CPU-type processing unit, a GPU-type processing unit, a field-programmable gate array (FPGA), another class of digital signal processor (DSP), or other hardware logic components that may, in some instances, be driven by a CPU. For example, and without limitation, illustrative types of hardware logic components that can be used include Application-Specific Integrated Circuits (ASICs), Application-Specific Standard Products (ASSPs), System-on-a-Chip Systems (SOCs), Complex Programmable Logic Device (CPLDs), etc.

A basic input/output system containing the basic routines that help to transfer information between elements within the computer architecture 1000, such as during startup, is stored in the ROM 1008. The computer architecture 1000 further includes a mass storage device 1012 for storing an operating system 1014, application(s) 1016, modules 1018, and other data described herein.

The mass storage device 1012 is connected to processing unit(s) 1002 through a mass storage controller connected to the bus 1010. The mass storage device 1012 and its associated computer-readable media provide non-volatile storage for the computer architecture 1000. Although the description of computer-readable media contained herein refers to a mass storage device, it should be appreciated by those skilled in the art that computer-readable media can be any available computer-readable storage media or communication media that can be accessed by the computer architecture 1000.

Computer-readable media can include computer-readable storage media and/or communication media. Computer-readable storage media can include one or more of volatile memory, nonvolatile memory, and/or other persistent and/or auxiliary computer storage media, removable and non-removable computer storage media implemented in any method or technology for storage of information such as computer-readable instructions, data structures, program modules, or other data. Thus, computer storage media includes tangible and/or physical forms of media included in a device and/or hardware component that is part of a device or external to a device, including but not limited to random access memory (RAM), static random-access memory (SRAM), dynamic random-access memory (DRAM), phase change memory (PCM), read-only memory (ROM), erasable programmable read-only memory (EPROM), electrically erasable programmable read-only memory (EEPROM), flash memory, compact disc read-only memory (CD-ROM), digital versatile disks (DVDs), optical cards or other optical storage media, magnetic cassettes, magnetic tape, magnetic disk storage, magnetic cards or other magnetic storage devices or media, solid-state memory devices, storage arrays, network attached storage, storage area networks, hosted computer storage or any other storage memory, storage device, and/or storage medium that can be used to store and maintain information for access by a computing device.

In contrast to computer-readable storage media, communication media can embody computer-readable instructions, data structures, program modules, or other data in a modulated data signal, such as a carrier wave, or other transmission mechanism. As defined herein, computer storage media does not include communication media. That is, computer-readable storage media does not include communications media consisting solely of a modulated data signal, a carrier wave, or a propagated signal, per se.

According to various configurations, the computer architecture 1000 may operate in a networked environment using logical connections to remote computers through the network 1020. The computer architecture 1000 may connect to the network 1020 through a network interface unit 1022 connected to the bus 1010. The computer architecture 1000 also may include an input/output controller 1024 for receiving and processing input from a number of other devices, including a keyboard, mouse, touch, or electronic stylus or pen. Similarly, the input/output controller 1024 may provide output to a display screen, a printer, or other type of output device.

It should be appreciated that the software components described herein may, when loaded into the processing unit(s) 1002 and executed, transform the processing unit(s) 1002 and the overall computer architecture 1000 from a general-purpose computing system into a special-purpose computing system customized to facilitate the functionality presented herein. The processing unit(s) 1002 may be constructed from any number of transistors or other discrete circuit elements, which may individually or collectively assume any number of states. More specifically, the processing unit(s) 1002 may operate as a finite-state machine, in response to executable instructions contained within the software modules disclosed herein. These computer-executable instructions may transform the processing unit(s) 1002 by specifying how the processing unit(s) 702 transition between states, thereby transforming the transistors or other discrete hardware elements constituting the processing unit(s) 1002.

FIG. 11 depicts an illustrative distributed computing environment 1100 capable of executing the software components described herein. Thus, the distributed computing environment 1100 illustrated in FIG. 11 can be utilized to execute any aspects of the software components presented herein. For example, the distributed computing environment 1100 can be utilized to execute aspects of the software components described herein.

Accordingly, the distributed computing environment 1100 can include a computing environment 1102 operating on, in communication with, or as part of the network 1104. The network 1104 can include various access networks. One or more client devices 1106A-1106N (hereinafter referred to collectively and/or generically as "clients 1106" and also referred to herein as computing devices 1106) can communicate with the computing environment 1102 via the network 1104. In one illustrated configuration, the clients 1106 include a computing device 1106A such as a laptop computer, a desktop computer, or other computing device; a slate or tablet computing device ("tablet computing device") 1106B; a mobile computing device 1106C such as a mobile telephone, a smart phone, or other mobile computing device; a server computer 1106D; and/or other devices 1106N. It should be understood that any number of clients 1106 can communicate with the computing environment 1102.

In various examples, the computing environment 1102 includes servers 1108, data storage 1110, and one or more network interfaces 1112. The servers 1108 can host various services, virtual machines, portals, and/or other resources. In the illustrated configuration, the servers 1108 host virtual machines 1114, Web portals 1116, mailbox services 1118, storage services 1120, and/or, social networking services 1122. As shown in FIG. 11 the servers 1108 also can host other services, applications, portals, and/or other resources ("other resources") 1124.

As mentioned above, the computing environment 1102 can include the data storage 1110. According to various implementations, the functionality of the data storage 1110 is provided by one or more databases operating on, or in communication with, the network 1104. The functionality of the data storage 1110 also can be provided by one or more servers configured to host data for the computing environment 1102. The data storage 1110 can include, host, or provide one or more real or virtual datastores 1126A-1126N (hereinafter referred to collectively and/or generically as "datastores 1126"). The datastores 1126 are configured to host data used or created by the servers 1108 and/or other data. That is, the datastores 1126 also can host or store web page documents, word documents, presentation documents, data structures, algorithms for execution by a recommendation engine, and/or other data utilized by any application program. Aspects of the datastores 1126 may be associated with a service for storing files.

The computing environment 1102 can communicate with, or be accessed by, the network interfaces 1112. The network interfaces 1112 can include various types of network hardware and software for supporting communications between two or more computing devices including, but not limited to, the computing devices and the servers. It should be appreciated that the network interfaces 1112 also may be utilized to connect to other types of networks and/or computer systems.

It should be understood that the distributed computing environment 1100 described herein can provide any aspects of the software elements described herein with any number of virtual computing resources and/or other distributed computing functionality that can be configured to execute any aspects of the software components disclosed herein. According to various implementations of the concepts and technologies disclosed herein, the distributed computing environment 1100 provides the software functionality described herein as a service to the computing devices.

It should be understood that the computing devices can include real or virtual machines including, but not limited to, server computers, web servers, personal computers, mobile computing devices, smart phones, and/or other devices. As such, various configurations of the concepts and technologies disclosed herein enable any device configured to access the distributed computing environment 1100 to utilize the functionality described herein for providing the techniques disclosed herein, among other aspects.

The present disclosure is supplemented by the following example clauses:

Example 1: A method for an artificial intelligence (AI) based recommendation system 100 associated with care or treatment of a patient, the method comprising: receiving (620) three-dimensional (3D) image data (116) associate with the patient, wherein the 3D image data (116) includes volumetric data; detecting (630) one or more anatomical treatment sites associated with the patient based on the received 3D image data (116); annotating (640) the 3D image data (116) with one or more of the detected anatomical treatment sites associated with the patient; evaluating (650) the 3D image data with a foundation model (140) to identify viable donor sites for flap harvesting; and providing a recommendation with the foundation model (140), where the recommendation includes one or more of the viable donor sites identified for flap harvesting based on a treatment criteria associated with treatment of the patient.

Example 2: The method of Example 1, further comprising: receiving the treatment criteria as an input to the AI based recommendation system, wherein the treatment criteria includes one or more of a functional objective, an aesthetic objective, and/or a risk factor objective.

Example 3: The method of any of the preceding examples, further comprising: receiving one or more prompts with the AI based recommendation system, where the prompts may be text based, image based, audio based, or combinations thereof; and providing the recommendation with the foundation model responsive to the received prompts, where the recommendation may be text based, image based, audio based, or combinations thereof.

Example 4: The method of Example 3, wherein receiving the one or more prompts comprises receiving one or more of the treatment criteria for treatment of the patient, patient medical records, marked images of the patient, and context data associated with identification and recommendation of viable donor sites.

Example 5: The method of any of the preceding examples, further comprising: capturing a plurality of images of the patient including the volumetric data; and forming the 3D image data by applying fusion of at least a portion of the plurality of images to in a three-dimensional (3D) model.

Example 6: The method of Example 5, wherein capturing the plurality of images comprises: capturing the plurality of images with a corresponding plurality of image capture devices, wherein each of the image capture devices is positioned at a different physical location with a different observation angle relative to the patient.

Example 7: The method of Example 5, wherein detecting one or more anatomical treatment sites comprises: evaluating the treatment criteria and the 3D image data associated with the patient; identifying one or more treatment sites associated with the treatment criteria; and estimating a volume of the identified treatment sites.

Example 8: The method of Example 7: wherein identifying one or more treatment sites associated with the treatment criteria comprises: identifying a tissue location of the patient that matches one or more of a functional objective, an aesthetic objective, or a risk factor objective.

Example 9: The method of Example 7, wherein identifying one or more treatment sites associated with the treatment criteria comprises: identifying a tissue location of the patient with a foundation model that identifies locations based on one or more of the treatment criteria, the 3D image data, and context data associated with locations of viable donor sites.

Example 10: The method of Example 5, wherein annotating the 3D image data comprises: evaluating the treatment criteria and the 3D image data associated with the patient; identifying one or more viable donor sites associated with the treatment criteria; and marking the identified donor sites in annotation data.

Example 11: The method of Example 10, further comprising: adding preliminary recommendations to the annotation data, where the preliminary recommendation includes one or more of text, images, audio, and/or meta-data.

Example 12: The method of any of the preceding examples, wherein providing the recommendation with the foundation model comprises: evaluating input sources associated with the patient, wherein the input sources corresponds to one or more of image data, detection data, annotation data, or treatment criteria associated with the patient; and generating recommendations for one or more of a flap site, a flap size, and a flap placement, and tissue details based on the evaluated input sources.

Example 13: The method of any of the preceding examples, wherein providing the recommendation with the foundation model comprises: evaluating input sources associated with the patient, wherein the input sources corresponds to one or more of image data, detection data, annotation data, or treatment criteria associated with the patient; generating recommendations for one or more of a flap site, a flap size, and a flap placement, and tissue details based on the evaluated input sources; and ranking the recommendations based on the treatment criteria, and generating an output based on the ranked recommendations, wherein the output comprises one or more of text, audio, images with markings, or combinations thereof.

Example 14: The method of any of the preceding examples, wherein providing the recommendation with the foundation model comprises: evaluating input sources associated with the patient, wherein the input sources corresponds to one or more of image data, detection data, annotation data, or treatment criteria associated with the patient; evaluating context data associated with one or more of reference anatomy data, reference defect image data, reference donor image data, and reference recommendations; and generating recommendations for one or more of a flap site, a flap size, and a flap placement, and tissue details based on the evaluated input sources and the evaluated context data.

Example 15: A computer-readable storage medium having computer-executable instructions stored thereupon that, when executed by one or more processing units of an AI based recommendation system (100) associated with care or treatment of a patient, cause the AI based recommendation system to: receive (620) three-dimensional (3D) image data (116) associate with the patient, wherein the 3D image data (116) includes volumetric data; detect (630) one or more anatomical treatment sites associated with the patient based on the received 3D image data (116);

annotate (640) the 3D image data (116) with one or more of the detected anatomical treatment sites associated with the patient; evaluate (650) the 3D image data with a foundation model (140) to identify viable donor sites for flap harvesting; and provide a recommendation with the foundation model (140), where the recommendation includes one or more of the viable donor sites identified for flap harvesting based on a treatment criteria associated with treatment of the patient.

Example 16: The computer-readable storage medium of Example 15, wherein the computer-executable instructions stored thereupon, when executed by one or more processing units of the AI based recommendation system, further cause the foundation model of AI based recommendation system to: evaluate input sources associated with the patient, wherein the input sources corresponds to one or more of image data, detection data, annotation data, or treatment criteria associated with the patient; and generate recommendations for one or more of a flap site, a flap size, and a flap placement, and tissue details based on the evaluated input sources.

Example 17: The computer-readable storage medium of Example 16, wherein the computer-executable instructions stored thereupon, when executed by one or more processing units of the AI based recommendation system, further cause the foundation model of AI based recommendation system to: rank the recommendations based on the treatment criteria, and generate an output based on the ranked recommendations, wherein the output comprises one or more of text, audio, images with markings, or combinations thereof.

Example 18. The computer-readable storage medium of Example 16, wherein the computer-executable instructions stored thereupon, when executed by one or more processing units of the AI based recommendation system, further cause the foundation model of AI based recommendation system to: evaluate context data associated with one or more of reference anatomy data, reference defect image data, reference donor image data, and reference recommendations; and adjust the recommendations based on the evaluated context data.

Example 19. The computer-readable storage medium of Example 16, wherein the computer-executable instructions stored thereupon, when executed by one or more processing units of the AI based recommendation system, further cause the foundation model of AI based recommendation system to: receive one or more prompts with the AI based recommendation system, where the prompts may be text based, image based, audio based, or combinations thereof; and provide revised recommendations with the foundation model responsive to the received prompts, where the revised recommendations may be text based, image based, audio based, or combinations thereof.

Example 20: An AI based recommendation system associated with care or treatment of a patient, the AI based recommendation system comprising: a processor; and a computer-readable storage medium having computer-executable instructions stored thereupon that, when executed by the processor, cause the AI based recommendation system to: receive (620) three-dimensional (3D) image data (116) associate with the patient, wherein the 3D image data (116) includes volumetric data; detect (630) one or more anatomical treatment sites associated with the patient based on the received 3D image data (116); annotate (640) the 3D image data (116) with one or more of the detected anatomical treatment sites associated with the patient; evaluate (650) the 3D image data with a foundation model (140) to identify viable donor sites for flap harvesting; and provide a recommendation with the foundation model (140), where the recommendation includes one or more of the viable donor sites identified for flap harvesting based on a treatment criteria associated with treatment of the patient.

While certain example embodiments have been described, these embodiments have been presented by way of example only and are not intended to limit the scope of the inventions disclosed herein. Thus, nothing in the foregoing description is intended to imply that any particular feature, characteristic, step, module, or block is necessary or indispensable. Indeed, the novel methods and systems described herein may be embodied in a variety of other forms; furthermore, various omissions, substitutions and changes in the form of the methods and systems described herein may be made without departing from the spirit of the inventions disclosed herein. The accompanying claims and their equivalents are intended to cover such forms or modifications as would fall within the scope and spirit of certain of the inventions disclosed herein.

It should be appreciated that any reference to "first," "second," etc. elements within the Summary and/or Detailed Description is not intended to and should not be construed to necessarily correspond to any reference of "first," "second," etc. elements of the claims. Rather, any use of "first" and "second" within the Summary, Detailed Description, and/or claims may be used to distinguish between two different instances of the same element.

In closing, although the various techniques have been described in language specific to structural features and/or methodological acts, it is to be understood that the subject matter defined in the appended representations is not necessarily limited to the specific features or acts described. Rather, the specific features and acts are disclosed as example forms of implementing the claimed subject matter.

What is claimed is:

1. A method for an artificial intelligence (AI) based recommendation system associated with care or treatment of a patient, the method comprising:
   receiving, via a chat-based user interface, a prompt requesting viable donor sites for flap harvesting;
   capturing a plurality of images of the patient with a corresponding plurality of image capture devices, wherein each of the plurality of image capture devices is positioned at a different physical location with a different observation angle relative to the patient;
   forming three-dimensional (3D) image data of the patient by fusion of at least a portion of the plurality of images in a 3D model, wherein the 3D image data of the patient includes volumetric data and the fusion aligns pixels of the portion of the plurality of images based on at least one of depth, color, or intensity;
   detecting a plurality of anatomical treatment sites associated with the patient based on the 3D image data of the patient;
   annotating the 3D image data of the patient with the plurality of anatomical treatment sites associated with the patient;
   evaluating the annotated 3D image data of the patient with a foundation model to identify the viable donor sites, for the flap harvesting, amongst the plurality of anatomical treatment sites associated with the patient; and
   displaying the recommendation based on the evaluating via the chat-based user interface, wherein the recommendation includes;
      the annotated 3D image data of the patient marking one or more of the viable donor sites identified, by the foundation model, for the flap harvesting based on a treatment criteria associated with the patient; and
      for each viable donor site of the one or more viable donor sites, a size of a flap to be harvested, a depth of the flap to be harvested, and a volume of the flap to be harvested.

2. The method of claim 1, further comprising receiving the treatment criteria as an input to the AI based recommendation system via the chat-based user interface, wherein the treatment criteria includes at least one of a functional objective, an aesthetic objective, or a risk factor objective.

3. The method of claim 1, wherein:
   the prompt is at least one of text based, image based, or audio based; and
   the recommendation is at least one of text based, image based, or audio based.

4. The method of claim 3, wherein receiving the prompt comprises receiving one or more of the treatment criteria for treatment of the patient, patient medical records, marked images of the patient, and context data associated with identification and recommendation of the viable donor sites.

5. The method of claim 2, further comprising identifying a tissue location of the patient that matches at least one of the functional objective, the aesthetic objective, or the risk factor objective.

6. The method of claim 1, further comprising identifying a tissue location of the patient with the foundation model based on at least one of the treatment criteria, the 3D image data, or context data associated with locations of the viable donor sites.

7. The method of claim 1, wherein annotating the 3D image data of the patient comprises adding preliminary recommendations to the 3D image data, where the preliminary recommendations include at least one of text, images, audio, or meta-data.

8. The method of claim 1, wherein the recommendation further includes tissue details.

9. A computer-readable storage medium having computer-executable instructions stored thereupon that, when executed by one or more processing units of an artificial intelligence (AI) based recommendation system associated with care or treatment of a patient, cause the AI based recommendation system to:

receive, via a chat-based user interface, a prompt requesting viable donor sites for flap harvesting;

capture a plurality of images of the patient with a corresponding plurality of image capture devices, wherein each of the plurality of image capture devices is positioned at a different physical location with a different observation angle relative to the patient;

form three-dimensional (3D) image data of the patient by fusion of at least a portion of the plurality of images in a 3D model, wherein the 3D image data of the patient includes volumetric data and the fusion aligns pixels of the portion of the plurality of images based on at least one of depth, color, or intensity;

detect a plurality of anatomical treatment sites associated with the patient based on the 3D image data of the patient;

annotate the 3D image data of the patient with the plurality of anatomical treatment sites associated with the patient;

evaluate the annotated 3D image data of the patient with a foundation model to identify the viable donor sites, for flap harvesting, amongst the plurality of anatomical treatment sites associated with the patient; and display the recommendation based on the evaluating via the chat-based user interface, wherein the recommendation includes:

the annotated 3D image data of the patient marking one or more of the viable donor sites identified, by the foundation model, for the flap harvesting based on a treatment criteria associated with the patient; and for each viable donor site of the one or more viable donor sites, a size of a flap to be harvested, a depth of the flap to be harvested, and a volume of the flap to be harvested.

10. The computer-readable storage medium of claim 9, wherein the recommendation further includes tissue details.

11. The computer-readable storage medium of claim 10, wherein the computer-executable instructions stored thereupon, when executed by the one or more processing units of the AI based recommendation system, further cause the foundation model of AI based recommendation system to:

evaluate context data associated with least one of reference anatomy data, reference defect image data, reference donor image data, and reference recommendations; and adjust the recommendation based on the context data.

12. The computer-readable storage medium of claim 10, wherein;

the prompt is at least one of text based, image based, or audio based; and the recommendation is at least one of text based, image based, or audio based.

13. An artificial intelligence (AI) based recommendation system associated with care or treatment of a patient, the AI based recommendation system comprising:

a processor; and a computer-readable storage medium having computer-executable instructions stored thereupon that, when executed by the processor, cause the AI based recommendation system to:

receive, via a chat-based user interface, a prompt requesting viable donor sites for flap harvesting;

capture a plurality of images of the patient with a corresponding plurality of image capture devices, wherein each of the plurality of image capture devices is positioned at a different physical location with a different observation angle relative to the patient;

form three-dimensional (3D) image data of the patient by fusion of at least a portion of the plurality of images in a 3D model, wherein the 3D image data of the patient includes volumetric data and the fusion aligns pixels of the portion of the plurality of images based on at least one of depth, color, or intensity;

detect a plurality of anatomical treatment sites associated with the patient based on the 3D image data of the patient;

annotate the 3D image data of the patient with the plurality of anatomical treatment sites associated with the patient;

evaluate the annotated 3D image data of the patient with a foundation model to identify the viable donor sites, for the flap harvesting, amongst the plurality of anatomical treatment sites associated with the patient; and display the recommendation based on the evaluating via the chat-based user interface, wherein the recommendation includes:

the annotated 3D image data of the patient marking one or more of the viable donor sites identified, by the foundation model, for the flap harvesting based on a treatment criteria associated with the patient; and for each viable donor site of the one or more viable donor sites, a size of a flap to be harvested, a depth of the flap to be harvested, and a volume of the flap to be harvested.

14. The AI based recommendation system of claim 13, wherein the computer-executable instructions further cause the AI based recommendation system to receive the treatment criteria as an input to the AI based recommendation system via the chat-based user interface, wherein the treatment criteria includes at least one of a functional objective, an aesthetic objective, or a risk factor objective.

15. The AI based recommendation system of claim 13, wherein:

the prompt is at least one of text based, image based, or audio based; and the recommendation is at least one of text based, image based, or audio based.

16. The AI based recommendation system of claim 15, wherein receiving the prompt comprises receiving the treatment criteria and patient medical records.

* * * * *